US005834193A

United States Patent [19]
Kozlowski et al.

[11] Patent Number: 5,834,193
[45] Date of Patent: Nov. 10, 1998

[54] METHODS FOR MEASURING TELOMERE LENGTH

[75] Inventors: Michael R. Kozlowski, Palo Alto, Calif.; Karen R. Prowse, Groningen, Netherlands; Sy-Shi Wang, Burlingame, Calif.; Sharon Wong; Nam Woo Kim, both of San Jose, Calif.; Richard Allsopp, Menlo Park, Calif.

[73] Assignee: Geron Corporation, Menlo Park, Calif.

[21] Appl. No.: 660,402

[22] Filed: Jun. 7, 1996

Related U.S. Application Data

[63] Continuation-in-part of Ser. No. 479,916, Jun. 7, 1995, abandoned.
[51] Int. Cl.⁶ .............................. C12Q 1/68; C07H 21/02; C07H 21/04
[52] U.S. Cl. ............................ 435/6; 536/24.31; 935/77; 935/78
[58] Field of Search ..................... 435/6, 91.2; 536/23.1, 536/24.3, 24.33; 935/77, 78

[56] References Cited

U.S. PATENT DOCUMENTS

| | | | |
|---|---|---|---|
| 4,737,454 | 4/1988 | Dattagupta et al. | ........................ 435/6 |
| 5,489,508 | 2/1996 | West et al. . | |

FOREIGN PATENT DOCUMENTS

| | | | |
|---|---|---|---|
| 2294322 | 4/1996 | United Kingdom | ............. C12Q 1/68 |
| 9323572 | 11/1993 | WIPO . | |
| 9408053 | 4/1994 | WIPO . | |
| 95/13381 | 5/1995 | WIPO | ............................ C12N 15/54 |
| 95/13382 | 5/1995 | WIPO | ............................ C12N 15/54 |

OTHER PUBLICATIONS

Feng et al., "The RNA Component of Human Telomerase", *Science* 269:1236–1241 (1995).
Farr et al., "Functional Reintroduction of Human Telomeres into Mammalian Cells", *PNAS* 88:7006–7010 (1991).
Brown et al., "Structure and Polymorphism of Human Telomere–Associated DNA", *Cell* 63:119–132 (1990).
Baird et al., "Mechanisms Underlying Telomere Repeat Turnover, Revealed by Hypervariable Variant Repeat Distribution Patterns in the Human Xp/Yp Telomere", *The EMBO Journal* 14:5433–5443 (1991).
Edwards et al., "Oligodeoxyribonucleotide Ligation to Single–Stranded cDNAs; a New Tool for Cloning 5' Ends of mRNAs and for Constructing cDNA Libraries by In Vitro Amplification", *Nucl. Acids Res.* 19:5227–5232 (1991).
Barany, "Genetic Disease Detection and DNA Amplification using Cloned Thermostable Ligase," *Proc. Natl. Acad. Sci. USA* 88:189–193 (1991).
Compton, "Nucleic Acid Sequence–Based Amplification", *Nature* 350:91–92 (1991).
Guatelli et al., "Isothermal, In Vitro Amplification of Nucleic Acids by a Multienzyme Reaction Modeled after Retroviral Replication",*Proc. Natl. Acad. Sci, USA* 87:1874–1878 (1990).

Walker et al., "Isothermal In Vitro Amplification of DNA by a Restriction Enzyme/DNA Polymerase System",*Proc. Natl. Acad. Sci. USA* 89:392–396 (1992).
Vaziri et al., "Loss of Telomeric DNA During Aging of Normal and Trisomy 21 Human Lymphocytes", *Am. J. Hum. Genet.* 52:661–667 (1993).
Counter et al., "Telomerase Activity in Normal Leukocytes and in Hematologic Malignancies", *Blood* 85:2315–2320 (1995).
Yamada et al., "Telomeric DNA in Normal and Leukemic Blood Cells", *J. Clin. Invest.* 95:1117–1123 (1995).
Garagna et al., "Robertsonian Metacentrics of the House Mouse Lose Telomeric Sequences but Retain some Minor Satellite DNA in the Pericentromeric Area," *Chromosoma* 103: 685–692 (1995).
Burgtorf et al., "A Telomere–Like Satellite $(GGGTCAT)_n$ Comprises 4% of Genomic DNA of Drosophila Hydei and is Located Mainly in Centromeric Heterochromatin of all Large Acrocentric Autosomes," *Gene* 137(2): 287–291 (1993).
Wright et al., "Modifications of a Telomeric Repeat Amplification Protocol (TRAP) Result in Increased Reliability, Linearity, and Sensitivity," *Nucleic Acids Research* 23: 3794–3795 (1995).
Kim et al., "Specific Association of Human Telomerase with Immortal Cells and Cancer" *Science* 266: 2011–2014 (1994).
Montgomery et al., "Genetic Instability of Chromosome 3 in HPV–Immortalized and Tumorigenic Human Keratinocytes", *Genes, Chromosomes, Cancer* 14:97–105 (1995).
Allsopp et al., "Telomere length predicts replicative capacity of human fibroblasts," *Proc. Natl. Acad. Sci. USA* 89:10114–10118 (1992).
Blackburn et al., "Recognition and Elongation of Telomeres by Telomerase," *Genome* 31: 553–560 (1989).
Blackburn, "Structure and Function of Telomeres," *Nature* 350:572 (1991).

(List continued on next page.)

*Primary Examiner*—Stephanie W. Zitomer
*Attorney, Agent, or Firm*—Kevin R. Kaster; Elaine C. Stracker

[57] ABSTRACT

Methods and compositions for the measurement of telomere length have application in medical diagnostic, prognostic, and therapeutic procedures. The methods for measuring telomere length include primer extension-based methods and probe-based methods. The primer extension methods involve elongation of telomeric, linker, and/or subtelomeric based primers under conditions such that the telomere serves as a template for primer extension and that the resultant primer extension products can be compared to standards of known length to provide a measure of telomere length. The probe based methods allow for telomere length measurements using DNA from lysed or whole cells and involve hybridizing an excess of probe to all telomeric repeat sequences in the telomere, measuring the amount of bound probe, and correlating the amount of bound probe measured with telomere length.

9 Claims, 4 Drawing Sheets

OTHER PUBLICATIONS

Blackburn, "The molecular structure of centromeres and telomeres," *Annual Reviews in Biochemistry* 53:163 (1984).

Cech, "Ribozymes and their medical implications," *J. of Amer. Med. Assoc.* 260:3030 (1988).

Cooke and Smith, "Variability at the telomeres of the human X/Y pseudoautosomal region," *Cold Harbor Symposia on Quantitative Biology* LI:213 (1986).

Cotten, "The in vivo application of ribozymes," *Trends in Biotechnology* 8:174–178 (1990).

Counter et al., "Stabilization of Short Telomeres and Telomerase Activity Accompany Immortalization of Epstein–Barr Virus–Transformed Human B Lymphocytes," *J. Virology* 68:3410–3414 (1994).

Counter et al., "Telomere shortening associated with chromosome instability is arrested in immortal cells which express telomerase activity," *EMBO J.* 11:1921–1929 (1992).

Counter et al., "Telomerase activity in human ovarian carcinoma," *Proc. Natl. Acad. Sci. USA* 91:2900–2904 (1994).

Eck and Nabel, "Antisense oligonucleotides for therapeutic intervention," *Current Opin. in Biotech* 2:897 (1991).

Gall, "Tying up loose ends," *Nature* 344:108 (1990).

Goldstein, "Replicative senescence: the human fibroblast comes of age," *Science* 249:1129 (1990).

Gottschling et al., "Position effect at *S. cerevisiae* telomeres: reversible repression of Pol II transcription," *Cell* 63:751 (1990).

Gray et al., "Cloning and expression of genes for the Oxytricha telomere–binding protein specific subunit interactions in the telomeric complex," *Cell* 67:807 (1991).

Greider, "Telomeres, telomerase and senescence," *Bioessays* 12:363 (1990).

Greider, "Chromosome first aid," *Cell* 67:645 (1991).

Greider et al., "Telomerase is Processive," *Molecular and Cellular Biology* 11:4572–4580 (1991).

Greider and Blackburn, "The telomere terminal transferase of tetrahymena is a ribonucleoprotein enzyme with two kinds of primer specificity," *Cell* 51:887–898 (1987).

Greider and Blackburn, "A telomeric sequence in the RNA of Tetrahymena telomerase required for telomere repeat synthesis," *Nature* 337:331–337 (1989).

Guo et al., "Interaction of the Dye Ethidium Bromide with DNA Containing Guanine Repeats," *Biochemistry* 31:2451–2455 (1992).

Ham and McKeehan, "Media and growth requirements," *Methods in Enzymology* LVIII:44 (1979).

Harley, "Telomere Loss: Mitotic Clock or Genetic Time Bomb?" *Nature* 256:271 (1991).

Harley, *Mutation Research* 256:271–282 (1991).

Harley et al., "The Telomere Hypothesis of Celluar Aging," *Expermiental Gerontology* 27:375–382 (1992).

Harley et al., "Telomeres Shorten During Ageing of Human Fibroblasts" *Nature* 345:458 (1990).

Harrington and Greider, "Telomerase primer specificity and chromosome healing," *Nature* 353:451 (1991).

Hayflick et al., "The serial cultivation of human diploid cell strains," *Experimental Cell Research* 25:585 (1961).

Hendersen et al., "Telomere G–strand structure and function analyzed by chemical protection, base analogue substitution, and utilization by telomerase in vitro," *Biochemistry* 29:732 (1990).

Henderson et al., "Structure, Synthesis and Regulation of Telomeres," *Cancer Cells* 6:453–461 (1988).

Jankovic et al., "Telomere loss and cancer," *Nature* 350:197 (1991).

Kafatos et al., "Determination of nucleic acid sequence homologies and relative concentrations by a dot hybridization procedure," *Nucleic Acids Research* 7:1541–1552 (1979).

Klingelhutz et al., "Restoration of Telomeres in Human Papoillomavirus–Immortalized Human Anogenital Epithelial Cells," *Molecular and Cellular Biology* 14:961–969 (1994).

Lundblad and Szostak, "A mutant with a defect in telomere elongation leads to senescence in yeast," *Cell* 57:633 (1989).

Morin, "The human telomere terminal transferase enzyme is a ribonucleoprotein that synthesizes TTAGGG repeats," *Cell* 59:521 (1989).

Muller et al., "New telomere formation after developmentally regulated chromosomal breakage during the process of chromosome diminution in *Ascaris lumbricoides*" *Cell* 67:815 (1991).

Ohno, "Strict relationship between dialyzed serum concentration and cellular life span" *Mechanisms of Aging and Development* 11:179 (1979).

Olovnikov, "A theory of marginotomy," *J. Theoretical Biology* 41:181 (1973).

Shay et al., "Loss of telomeric DNA during aging may predipose cells to cancer (Review)," *Int'l J. Oncology* 3:559–563 (1993).

Smith et al., "Intraclonal variation in proliferative potential of human diploid fibroblasts: stochastic mechanisms for cellular aging," *Science* 207:82 (1980).

Starling et al., "Extensive telomere repeat arrays in mouse are hypervariable," *Nucleic Acids Research* 18:6881 (1990).

Strahl and Blackburn, "The effects of nucleoside analogs on telomerase and telomeres in Tetrahymena," *Nucleic Acids Research* 22:893–900 (1994).

Szostak, "The beginning of the ends," *Nature* 337:303 (1989).

Wang and Zakian, "Telomere–telomere recombination provides an express pathway for telomere acquisition," *Nature* 345:456 (1990).

Windle and McGuire, "Telomeres: the long and the short of it," *Proceedings of the American Association for Cancer Research* 33:594–595 (1992).

Yu et al., "In vivo alteration of telomere sequences and senescence caused by mutated Tetrahymena telomerase RNAs," *Nature* 344:126 (1990).

Yu et al., "Developmentally Programmed Healing of Chromosomes by Telomerase in Tetrahymena," *Cell* 67:823 (1991).

Zahler et al., "Inhibition of Telomerase by G–quartet DNA Structures," *Nature* 350:718–720 (1991).

| Mean TRF Values (kb) | |
|---|---|
| S2C Cells | |
| Lane | Mean TRF |
| 1 | 8.57 |
| 2 | 8.55 |
| 3 | 7.87 |
| 4 | 8.70 |
| 5 | 8.93 |
| 6 | 8.51 |
| 7 | 10.74 |
| BJ Cells | |
| Lane | Mean TRF |
| 8 | 6.96 |
| 9 | 7.17 |
| 10 | 7.71 |
| 11 | 8.25 |
| 12 | 7.96 |
| 13 | 7.63 |
| 14 | 8.33 |
| 15 | 8.62 |
| 16 | 8.85 |
| 17 | 9.40 |
| 18 | 9.63 |

| A | B | C |
|---|---|---|
| BJ 27.5 | BJ 80.0 | BJ 82.2 |
| BJ 28.6 | BJ 73.5 | BJ 91.4 |
| BJ 41.2 | BJ 72.2 | S2C 30.0 |
| BJ 46.6 | BJ 69.2 | S2C 39.0 |
| BJ 57.2 | BJ 57.2 | S2C 44.0 |
| BJ 69.2 | BJ 41.2 | S2C 47.0 |
| BJ 72.2 | BJ 28.6 | S2C 53.0 |
| BJ 73.2 | BJ 27.5 | S2C 62.0 |
| BJ 80.0 | Rep4 0.0015625 | S2C 69.2 |
| BJ 82.2 | λHdIII +Sau3A | S2C 71.2 |
| BJ 91.4 | Rep4 0.003125 | S2C 73.2 |
| S2C 30.0 | Rep4 0.00625 | Rep4 0.0125 |
| S2C 39.0 | Rep4 0.00625 | Rep4 0.009375 |
| S2C 44.0 | Rep4 0.009375 | Rep4 0.00625 |
| S2C 47.0 | S2C 73.2 | Rep4 0.003125 |
| S2C 53.0 | S2C 71.2 | Rep4 0.0015625 |
| S2C 62.0 | S2C 69.2 | λHdIII +Sau3A |

FIG. 3B

SEQUENCE LISTING ( 1 ) GENERAL INFORMATION:

( i i i ) NUMBER OF SEQUENCES: 13

( 2 ) INFORMATION FOR SEQ ID NO: 1:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) SEQUENCE DESCRIPTION: SEQ ID NO: 1:

TGCAATTATT TTACTATCTG TTATCGG      27

( 2 ) INFORMATION FOR SEQ ID NO: 2:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 2:

TGACCTGTTT TAAAGAGTAT GCTCAG      26

( 2 ) INFORMATION FOR SEQ ID NO: 3:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 3:

CCCTCTGAAA GTGGACCWAT CAG      23

( 2 ) INFORMATION FOR SEQ ID NO: 4:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 4:

CTTTTATTCT CTAATCTGCT CCC      23

( 2 ) INFORMATION FOR SEQ ID NO: 5:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 5:

TAGGGGTTGT CTCAGGGTCC TA      22

( 2 ) INFORMATION FOR SEQ ID NO: 6:

( i ) SEQUENCE CHARACTERISTICS:
    ( A ) LENGTH: 23
    ( B ) TYPE: nucleic acid
    ( C ) STRANDEDNESS: single
    ( D ) TOPOLOGY: linear ( i i ) SEQUENCE DESCRIPTION: SEQ ID NO: 6:

GGGAGCAGAT TAGAGAATAA AAG    23

( 2 ) INFORMATION FOR SEQ ID NO: 7:

( i ) SEQUENCE CHARACTERISTICS:
    ( A ) LENGTH: 23
    ( B ) TYPE: nucleic acid
    ( C ) STRANDEDNESS: single
    ( D ) TOPOLOGY: linear ( i i ) SEQUENCE DESCRIPTION: SEQ ID NO: 7:

CTGATWGGTC CACTTTCAGA GGG    23

( 2 ) INFORMATION FOR SEQ ID NO: 8:

( i ) SEQUENCE CHARACTERISTICS:
    ( A ) LENGTH: 24
    ( B ) TYPE: nucleic acid
    ( C ) STRANDEDNESS: single
    ( D ) TOPOLOGY: linear ( i i ) SEQUENCE DESCRIPTION: SEQ ID NO: 8:

GGAATTCTGG TCGACGGATC CTGA    24

( 2 ) INFORMATION FOR SEQ ID NO: 9:

( i ) SEQUENCE CHARACTERISTICS:
    ( A ) LENGTH: 24
    ( B ) TYPE: nucleic acid
    ( C ) STRANDEDNESS: single
    ( D ) TOPOLOGY: linear ( i i ) SEQUENCE DESCRIPTION: SEQ ID NO: 9:

TCAGGATCCG TCGACCAGAA TTCC    24

( 2 ) INFORMATION FOR SEQ ID NO: 10:

( i ) SEQUENCE CHARACTERISTICS:
    ( A ) LENGTH: 17
    ( B ) TYPE: nucleic acid
    ( C ) STRANDEDNESS: single
    ( D ) TOPOLOGY: linear ( i i ) SEQUENCE DESCRIPTION: SEQ ID NO: 10:

CCGTCGACCA GAATTCC    17

( 2 ) INFORMATION FOR SEQ ID NO: 11:

( i ) SEQUENCE CHARACTERISTICS:
    ( A ) LENGTH: 17
    ( B ) TYPE: nucleic acid
    ( C ) STRANDEDNESS: single
    ( D ) TOPOLOGY: linear ( i i ) SEQUENCE DESCRIPTION: SEQ ID NO: 11:

CAGGATCCGT CGACCAG    17

( 2 ) INFORMATION FOR SEQ ID NO: 12:

( i ) SEQUENCE CHARACTERISTICS:
    ( A ) LENGTH: 24

(B) TYPE: nucleic acid
           (C) STRANDEDNESS: single
           (D) TOPOLOGY: linear (ii) SEQUENCE DESCRIPTION: SEQ ID NO: 12:

CCCTAACCCT AACCCTAACC CTAA                                                                    24

(2) INFORMATION FOR SEQ ID NO: 13:

(i) SEQUENCE CHARACTERISTICS:
           (A) LENGTH: 18
           (B) TYPE: nucleic acid
           (C) STRANDEDNESS: single
           (D) TOPOLOGY: linear (ii) SEQUENCE DESCRIPTION: SEQ ID NO: 13:

TTAGGGTTAG GGTTAGGG                                                                           18

METHODS FOR MEASURING TELOMERE LENGTH

CROSS-REFERENCE TO RELATED APPLICATION

The present application is a continuation-in-part of U.S. patent application Ser. No. 08/479,916, filed Jun. 7, 1995, now abandoned.

BACKGROUND OF THE INVENTION

1. Field of Invention

The present invention relates to methods and reagents for the measurement of telomere length. The invention has applications in the fields of molecular biology, cell culture technology, and medical therapeutics and diagnostics technology.

2. Description of Related Disclosures

Telomeres are specialized nucleoprotein structures at the ends of chromosomes that are important in maintaining chromosome stability and function (Blackburn, 350 *Nature* 569, 1991; all references cited herein are incorporated by reference herein). Telomeres function through prevention of aberrant recombination and degradation at the ends of the chromosomes (Henderson et al., 29 *Biochemistry* 732, 1990; Bourgain et al., 19 *Nucl. Acids Res.* 1541, 1991), organization of the sub-nuclear architecture (Gilson et al., 3 *Trends Cell Biol.* 128, 1993), and involvement in the transcriptional suppression of genes at distal loci (Sen et al., 334 *Nature* 410, 1988). Telomeres are typically composed of a tandem repetitive array of a short sequence.

In humans, the telomeres are composed of many kilobases of simple tandem 5'-TTAGGG repeats (Moyzis et al., 85 *Proc. Natl. Acad. Sci. U.S.A.* 6622, 1988). These repeats are arranged such that the G-rich strand runs 5' to 3' towards the end of the chromosome and sometimes extends beyond the 5' end to generate a single-stranded 5'-(TTAGGG)$_n$ overhang, where n is typically 9 to 35 (but n can be more than 35 or less than 9). During DNA synthesis, the termini of the chromosomes are not fully replicated (Watson, 239 *Nature New Biology* 197, 1972) by the action of DNA polymerase. Incomplete replication occurs at the 3' end of each of the two template strands of the chromosome, because the RNA primer needed to initiate synthesis in effect masks the 3' end of the template. The RNA primer is degraded after strand synthesis, and, as there are no additional sequences beyond the 3' end of the template to which primers can anneal, the portion of the template to which the RNA primer hybridized is not replicated. In the absence of other enzymes, the chromosome is thus shortened with every cell division. This phenomena is referred to as the "end-replication problem" and is believed to be a key factor in the onset of cellular senescence and aging.

Evidence for this end-replication problem was provided by demonstrating that, in normal human somatic cells (e.g., fibroblasts, endothelial, and epithelial cells), telomeres shorten by 50–200 bp with each cell doubling (Harley et al., 345 *Nature* 458, 1990; Allsopp et al., 89 *Proc. Natl. Acad. Sci. U.S.A.* 10114, 1992). As a consequence, all normal human somatic cells have a limited capacity to proliferate, a phenomenon that has come to be known as the Hayflick limit, after which the cells enter replicative senescence. In human fibroblasts, this limit occurs after 50–100 population doublings, after which the cells remain in a viable but quiescent state for many months. See, Goldstein, 249 *Science* 1129, 1990.

Cellular immortalization (the acquisition of unlimited replicative capacity) is an abnormal escape from cellular senescence. See, Shay et al., 196 *Exp. Cell Res.* 33, 1991. Cells can escape from cellular senescence by adding telomeric DNA to the telomeres to overcome the end-replication problem. Most eukaryotic species utilize a novel enzyme, telomerase, to generate telomeric DNA de novo, thus compensating for, rather than avoiding terminal deletions of telomeric repeat sequences. The enzyme human telomerase can add 5'-TTAGGG repeats to the 3' end of telomeric DNA, thus extending the DNA and preventing telomere shortening.

Telomerase is a complex of protein components and an integral RNA component. The RNA component of the human enzyme contains a short region complementary to the human telomeric repeat sequence (Feng et al., 269 *Science* 1236, 1995). This complementary sequence allows the telomerase RNA to serve as a template for the catalytic extension of the 3' telomeric termini (Greider et al., 337 *Nature* 331, 1989).

Cycles of elongation and translocation allow human telomerase to extend processively the 3' region of chromosomes with 5'-TTAGGG repeats.

Telomere shortening occurs systematically with each cell division, and telomerase activation stabilizes telomeres; therefore, knowledge of the telomere length and the presence or lack of telomerase activity can provide information about the replicative history and the proliferative potential of cells. Harley, 256 *Mutation Research* 271, 1991, suggests that telomeres may act as a mitotic clock. The progressive shortening of telomeres can be viewed as the means by which cells count divisions; a sufficiently short telomere(s) can signal replicative senescence in normal cells (Wright and Shay, 8 *Trends Genetics* 193, 1992).

U.S. Pat. No. 5,489,508, issued Feb. 2, 1996; PCT Pub No. 95/13381, published May 18, 1995; and PCT Pub. No. 95/13382, published May 18, 1995, describe, inter alia methods by which the length of telomeres can be measured.

One approximate measure of telomere length, the length in nucleotides of the sum of all telomeric repeat sequences, is the length of a "terminal restriction fragment" (TRF). The TRF is defined as the length (or average length) of fragments generated by complete digestion of the genomic DNA with a restriction enzyme that does not cleave nucleic acids composed entirely of tandem arrays of the specific telomeric repeat sequence of interest. These large fragments can, depending on the restriction enzyme used and the source of the telomeric DNA, comprise both telomeric repeats and also "subtelomeric" DNA. Subtelomeric DNA is composed of DNA sequences adjacent to the tandem telomeric repeat sequences and generally contains telomeric repeat sequences interspersed with variable telomere-like sequences (Cross et al., 18 *Nucl. Acid Res.* 6649, 1990; deLange et al., 10 *Mol. Cell Biol.* 518, 1990; Brown et al., 63 *Cell* 119, 1990). Mean TRF length can provide a measure of telomere length of telomeres in a cell or a cell population.

TRF length measurement entails digesting genomic DNA with a restriction enzyme, typically one with a four-base recognition sequence (e.g., AluI, HinfI, MspI, RsaI, and Sau3A), used individually or in combination. This digestion results in the production of short fragments of non-telomeric DNA and longer fragments of telomeric DNA. The digested DNA is electrophoresed, and a Southern blot is performed by hybridizing the DNA to a radiolabeled telomeric probe, such as for human telomeres, 5'-(TTAGGG)$_3$ or 5'-(CCCTAA)$_3$. The telomeric DNA can then be visualized by autoradiography and mean lengths of terminal restriction fragments calculated from densitometric scans using computer programs known in the art. See, Harley et al., 345 *Nature* 458, 1990.

Another method for telomere length measurement (see PCT Pub. No. 95/13882, supra) involves the synthesis of DNA complementary to the telomeres of genomic DNA. The synthesized DNA can be labeled or unlabeled, and the length of this DNA can be determined by gel electrophoresis or other techniques known in the art. Alternatively, telomere length can be measured by the "anchored terminal primer" method, or by a modified Maxam-Gilbert reaction (see PCT Pub. No. 95/13382, supra). These two techniques provide for a more direct measurement of telomere length by exclusion of "the subtelomeric region" in the analysis.

Telomere length serves as a biomarker for cell turnover. Thus, information on the relative age, proliferative capacity, and other cellular characteristics associated with telomere and telomerase status can be obtained by measuring telomere length. Measurement of telomere length can be used to diagnose and stage cancer and other diseases as well as cell senescence. Other applications for telomere length measurement include determining the efficacy of treatment with a telomere length modulating compound (Feng et al., 269 *Science* 1236, 1995); discovering agents that modulate telomere length, telomerase activity, or the rate of telomere loss; and determining the presence of telomerase activity.

There remains a need for more rapid, reliable, accurate, and efficient methods for measuring telomere length so that the full potential of such applications can be realized. This invention meets this and other needs.

SUMMARY OF THE INVENTION

The present invention provides improved methods for measuring telomere length. The methods of the invention can be performed rapidly and provide increased sensitivity, efficiency, reliability, and accuracy. Moreover, these methods are amenable to automation and high through-put formats and provide, in some embodiments, a means to measure the telomere length of an individual chromosome, to compare interchromosomal variance in telomere length, and to measure telomere length of a specific cell population within a mixture of cells. In addition, the methods allow one to sort cells and/or chromosomes on the basis of telomere length. The present invention provides numerous advantages over the conventional method of telomere length measurement.

In one aspect of the invention, a method for measuring telomere length is provided that comprises the steps of:
  (a) covalently attaching an oligonucleotide linker to a telomere for which a measure of length is desired;
  (b) contacting a primer comprising a sequence sufficiently complementary to said linker to hybridize specifically thereto under conditions such that said primer extends to form a primer extension product complementary to said telomere; and
  (c) correlating telomere length with primer extension product size, thereby providing a measure of telomere length.

In one embodiment, the method involves replication or amplification of the telomere sequences by, for example, "polymerase chain reaction" (PCR) amplification. A product defined by extension of two primers, a "forward" primer complementary in sequence to the linker covalently bound to the 3' end of the telomere and a second primer complementary to a subtelomeric region of the chromosome, is exponentially amplified by this method. This method provides an accurate and sensitive measurement of the telomere length. In a preferred embodiment of this method, a double-stranded oligonucleotide linker is used, and prior to the ligation of the linker, the chromosomal DNA is treated with a nuclease to generate blunt ends to improve ligation. Those of skill in the art will recognize that the use of two primers for the extension step provides for exponential amplification but that linear amplification, with a single primer, can also be used to determine telomere length in accordance with the method of the invention.

Another embodiment of the primer extension method of the invention provides a rapid means for measuring telomeres using only one primer. In this method, a primer complementary to the covalently bound linker is extended using a polymerase and either (i) only those nucleotides complementary to the nucleotides in the telomeric repeat; or (ii) those nucleotides and a nucleotide analog known as a chain terminator, such as a dideoxynucleotide. One or more of the nucleotides can be labeled. For human telomeres, exclusion of dGTP and/or addition of dideoxy GTP (ddGTP) nucleotide results in termination of primer extension at the first C nucleotide relative to the 3' end of the G-rich strand of the chromosome. Denaturation and repeated cycles of primer extension and denaturation result in multiple copies of the telomeric region. One then measures the size of the extension products to estimate telomere length. For example, if one uses a labeled nucleotide, and the label is a radioactive label, one can measure telomere length by correlating scintillation counts of labeled nucleotide incorporated into primer extension products with telomere length.

In another aspect of the invention, one can optionally dispense with the linker altogether. In one alternate embodiment of this method, a subtelomeric primer is used as the sole primer, eliminating the need for ligating or otherwise covalently attaching a linker to the 3' end of the telomere. As noted above, repeated steps of primer extension and denaturation generate multiple single-stranded copies of the telomeric region. In another alternate embodiment, nucleotide analogs known as chain terminators are employed in the primer extension step. This method comprises the steps of:
  (a) contacting double-stranded chromosomal DNA in a sample with a primer having a sequence sufficiently complementary to a 3' end of a telomere to hybridize therewith in the presence of a mixture of nucleotides and a dideoxynucleotide under conditions such that said primer extends to form a primer extension product terminating with said dideoxynucleotide; and
  (b) correlating telomere length with primer extension product size to provide a measure of telomere length.

In this embodiment, the use of a specific dideoxynucleotide in the primer extension step provides a means to replicate only the telomeric portion of the chromosome. The dideoxynucleotide selected depends on the telomeric repeat sequence and the particular strand of the telomere that will serve as the template for primer extension. One selects a dideoxynucleotide that will not be incorporated until the primer has been extended past the telomeric region. Incorporation of a labeled nucleotide or dideoxynucleotide into the extension product, or probe-based identification of the extension products on a gel, provides a means to determine extension product size, which correlates with telomere length.

In another aspect of the invention, one can avoid the use of labeled nucleotides and gel electrophoresis by employing labeled probes to measure telomere length. This method comprises the steps of:

(a) contacting denatured chromosomal DNA with a labeled probe having a sequence complementary to a telomere repeat sequence under conditions such that said probe hybridizes specifically to telomeric DNA;

(b) measuring amount of bound probe; and (c) correlating said amount of bound probe measured with telomere length.

As noted above, this method does not require the use of gels, as in the conventional assay for telomere length determination, and is conducive to high through-put or automated processes, which is especially useful for clinical applications. In a preferred embodiment, the analysis of telomere length utilizes imaging techniques that allow for not only intercellular and intracellular telomere length determination and comparison, but also the separation of cells or chromosomes based on telomere length.

The methods of the invention are broadly applicable to the measurement of telomere length in any sample from any origin. The methods are especially useful and applicable to the measurement of telomere length in samples of biological material obtained from humans. Such samples will contain cells or cellular materials and will typically be obtained from humans for the purposes of determining remaining proliferative capacity or lifespan of the cells in the sample, diagnosing medical conditions, or identifying disease or proliferative states. These and other aspects of the invention are described in more detail below, beginning with a brief description of the accompanying drawings.

BRIEF DESCRIPTION OF THE DRAWINGS

FIGS. 3A and 3B show a comparison of mean TRF length (in b) analysis by the conventional method (FIG. 3A) for S2C and BJ cells at various population doubling levels (PDL), from higher PDL (lanes 1 and 8, FIG. 3A) to lower PDL (lanes 7 and 18, FIG. 3A), with the slot-blot method (FIG. 3B), a variation of the dot-blot method. In FIG. 3B, each row shows the amount of probe bound for cells at a certain PDL or to control DNA ($\lambda$HdIII+Sau3A is the negative control and Rep4 is the positive control) of varying amounts, as shown in the key to the Figure, all as described in more detail in Example 2.

DESCRIPTION OF THE PREFERRED EMBODIMENTS

Figure 1:
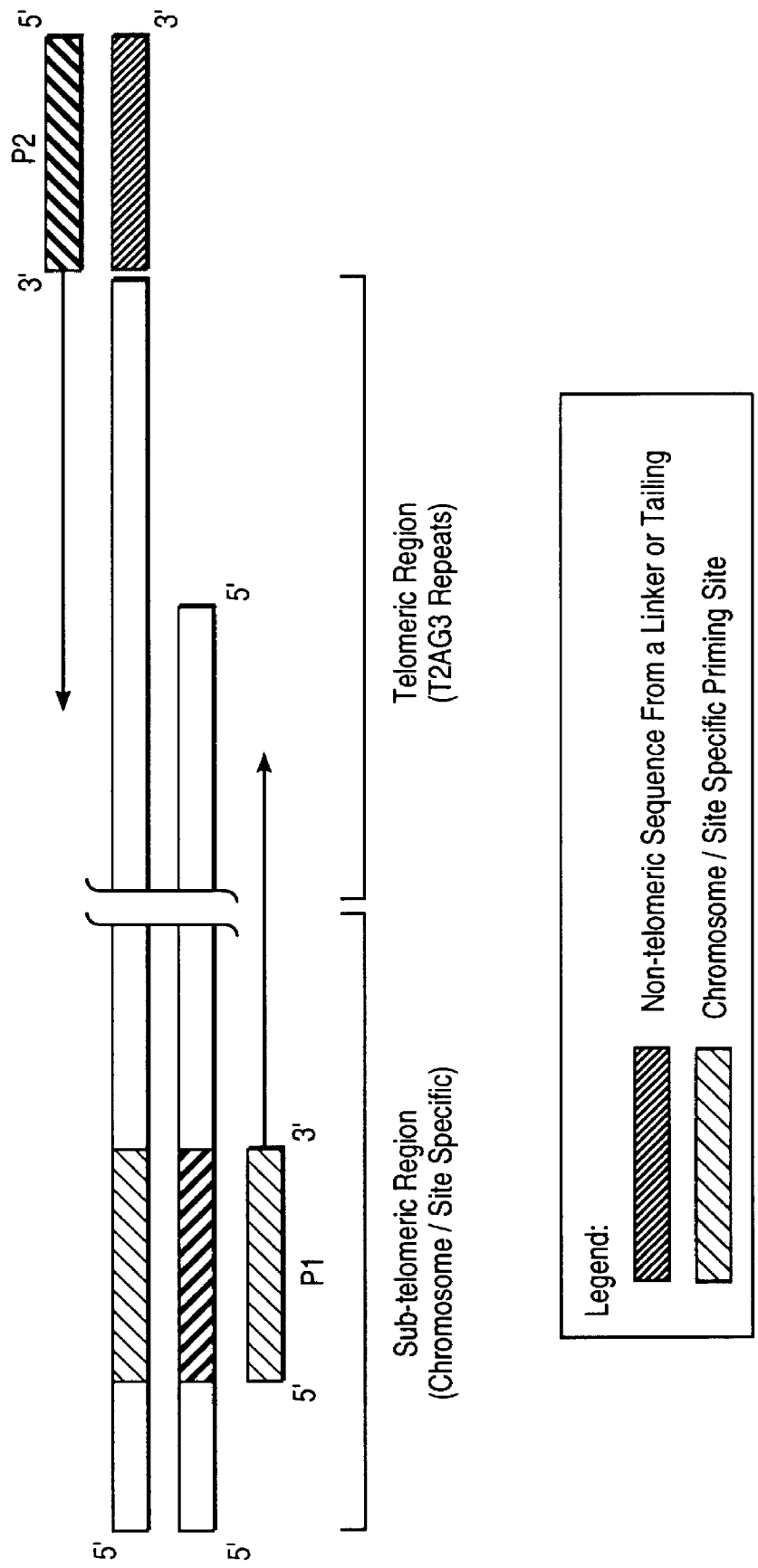
FIG. 1 illustrates a PCR-based telomere length measurement using a linker ligated or attached by tailing to the telomere, a primer complementary in sequence to the linker, and a subtelomeric primer.

The present invention provides improved methods for measuring telomere length. Telomeres are nucleoprotein structures at the ends of chromosomes and have been shown to function in chromosomal stabilization, position, and replication. Telomeres are also believed to serve as the mitotic clock for signaling cellular senescence. Because chromosomes of normal somatic cells have been shown to lose about 50–200 nucleotides of telomeric sequence per cell division, telomere length measurement provides a means for determining the proliferative lifespan of a cell. Numerous diseases are characterized by accelerated cell proliferation (hyperproliferative states) or decreased proliferative capacity. Therefore, improved telomere length measurements help meet the need for improved diagnostic and prognostic methodology.

To facilitate understanding of the invention, the disclosure of the invention is organized in sections as follows. First, a definition section is provided to define terms and phrases used commonly throughout the disclosure. This definition section includes a comprehensive description of the types of samples, primers, probes and labels that can be used with the invention. The next section describes methods of the invention for measuring telomere length. The methods for measuring telomere length are divided into two major categories, primer extension based methods and probe based methods. The probe based methods section is further subdivided to describe telomere length measurements using DNA from lysed cells and using whole cells. Then, various applications of the invention are described; this description is followed by detailed examples illustrating the invention.

DEFINITIONS

To assist in the understanding of the invention, the following terms as used herein are defined below.

"Abnormal chromosome" means a chromosome which has undergone a deletion, addition, or translocation such that the telomeric region is adjacent to chromosomal DNA not normally adjacent to the telomere.

"Blot" means a DNA-binding filter or substrate, such as nitrocellulose or a Silent Monitor™ Biodyne B membrane.

"Branched DNA probe" or "bDNA probe" means a probe designed for branched DNA signal amplification (Urdea, 12 BioTech. 926, 1994; U.S. Pat. No: 5,124,246), which involves amplification of the signal produced upon probe hybridization to a target nucleic acid. The bDNA probe is comprised of a hybridizing portion complementary to the telomeric repeats (e.g., 5'-(CCCTAA)$_n$-3' or its permutations, where n comprises 8 or more nucleotides in length, preferably 12 to 15 to 20 or more nucleotides in length), and so hybridizes with telomeric nucleic acid. The probe further comprises a branched region that provides multiple secondary probe binding sites. After washing to remove unbound probe, a labeled secondary probe specific for the branches of the bDNA is hybridized to the bDNA and is detected via the label. The signal increases in direct proportion to the secondary probe-accessible-sites on the bDNA molecule; thus a rare population of target nucleic acids can be detected by bDNA hybridization. Sensitivity can be further enhanced by probing the telomeric-repeat-complementary-bDNA with a secondary bDNA probe specific for the branches of the primary bDNA probe (and a tertiary probe specific for the secondary probe, and so on), thereby presenting more numerous hybridization sites for the labeled probe. PNA probes as well as other modified nucleic acid robes, can also be used as bDNA probes.

"Change in telomere length" means that the average or mean telomere length of chromosomal DNA in a particular cell population or sample is increased or decreased relative to other normal somatic cells in an individual or relative to normal somatic cells in other individuals, i.e., those not suffering from a disease condition.

"Label" means a chemical used to facilitate identification and/or quantitation of a target substance. Illustrative labels include fluorescent (e.g., FITC or rhodamine), phosphorescent, chemiluminescent, enzymatic, and radioactive labels, as well as chromophores. Any of a wide variety of labeled reagents can be used for purposes of the present invention. For instance, one can use one or more labeled nucleoside triphosphates, primers, linkers, or probes in the methods of the invention. The term label can also refer to a "tag" that can bind specifically to a labeled molecule. For instance, one can use biotin as a tag and then use avidinylated or streptavidinylated horseradish peroxidase (HRP) to bind to the tag, and then use a chromogenic substrate (e.g., tetramethylbenzamine) to detect the presence of HRP. In a similar fashion, the tag can be an epitope or antigen (e.g., digoxigenin), and an enzymatically, fluorescently, or radio-actively labeled antibody can be used to bind to the tag. For purposes of the present invention, the telomeric repeat itself can be a tag. Telomeric repeat binding proteins are known in the art and bind to either double-stranded or single-stranded telomeric repeats. If the labeling method involves the use of a protein, then native or recombinant proteins can be used; typically, such proteins would be purified for use and detected by virtue of a label attached to the particular protein or an antibody specific for the particular protein.

"Linker" means a single- or double-stranded oligonucleotide composed of nucleotides that is to be ligated to another oligonucleotide or nucleic acid.

"Linker sequence" means the nucleotide sequence of a linker.

"Long polymerase chain reaction (PCR)" means PCR amplification conditions suitable for amplification of a relatively large nucleic acid (see Cheng, "Efficient PCR of Long Targets", *New Horizons in Gene Amplification Technologies: New Techniques and Applications;* San Francisco, Calif. (1994)); typically, the amplified nucleic acid has a length greater than about 200 nucleotides, but the use of the word "long" is not intended to limit the length of the nucleic acid that can be amplified.

"Metaphase spread" refers to a cluster of chromosomes that are derived from cells that have been blocked in metaphase as a result of growth in the presence of a spindle formation inhibitor, such as colcemid. The cell is treated with a hypotonic buffer to cause swelling and burst upon dropping on a surface. Upon bursting, the chromosomes are released out of the cell and disperse onto the surface in clusters. Typically, the chromosomes are spread out on a microscope slide to facilitate visualization and microscopic analysis.

"Modified rate of telomere loss" means an increase or decrease in telomere loss over a defined time period (e.g., a year) or biological occurrence (e.g., a population doubling) relative to other normal somatic cells in that individual, or to normal somatic cells in other individuals, i.e., individuals not suffering from a disease condition.

"Oligonucleotide" means a molecule consisting of covalently linked naturally occurring or synthetically constructed nucleotides and/or nucleotide analogs. As used in this disclosure, oligonucleotides are generally primers, probes, and linkers composed of deoxyribonucleotides. However, the oligonucleotides of the invention can also be composed of ribonucleotides, modified analogs of ribo- or deoxyribonucleotides (i.e., synthetic or non-naturally occurring), or mixtures of any of the same. Usually, nucleotide monomers in an oligonucleotide are linked by phosphodiester bonds. However, as will be apparent to one in the art, alternate linkages can be used, including phosphorothioate, phosphorodithioate, phosphoroselenate, phosphorodiselenoate, phosphoranilidate, phosphoroamidate, peptide, and the like linkages. For example, a peptide nucleic acid (PNA) is an oligonucleotide with peptide bonds instead of phosphodiester bonds. Because a PNA has no charge, a PNA has a higher binding affinity than a deoxyribonucleic acid.

"Primer" means an oligonucleotide designed to hybridize to a target nucleic acid and then be extended by the addition of nucleotides or an oligonucleotide. A primer is typically extended by action of a polymerase or ligase. Typically, an oligonucleotide primer will be 8 or more nucleotides in length, preferably 12 to 15 to 20 or more nucleotides in length.

"Probe" means an oligonucleotide designed to hybridize specifically with a target nucleic acid. Because human telomeres comprise repeats of sequence 5'-TTAGGG-3', a telomeric probe, unless otherwise indicated, will be identical or complementary to a sequence contained within a sequence of two or more such repeats, i.e., the probe will comprise a sequence such as 5'-CCCTAA-3', (for an RNA probe, 5'-CCCUAA-3'), or 5'-CTAACC-3', for example. Typically, an oligonucleotide probe will be 8 or more nucleotides in length, preferably 12 to 15 to 20 or more nucleotides in length.

"Proliferative capacity" means the inherent ability of a cell or cells in a tissue to divide for a number of divisions (the "Hayflick" limit) under normal proliferation conditions.

"Riboprobe" means a probe comprised of ribonucleotides. A telomeric riboprobe can be produced by transcription of multiple, tandem telomere repeat sequences in a recombinant host cell, typically *E.coli,* as described in Example 1.

"Sample" means a composition of matter comprising a cell or cell extract. The methods of the present invention can be applied to any type of sample. Samples of particular interest include cell samples such as normal or diseased tissue samples, e.g., tumor samples, obtained for purposes of diagnostic or prognostic analysis. For diagnosis, telomere length measurement may be performed on a particular cell type, on all cells in a tissue (where various cell types may be present), or on extracts of a cell or cells where extract refers to a whole cell extract or a subfraction thereof, such as a specific chromosome from a cell. Typically, but not in all instances, the sample is treated to render the telomeric DNA in the cells more accessible. The preparation of the DNA can be accomplished by any of a variety of methods, depending upon the method for measuring telomere length to be employed.

"Senescent state" means that state in which a cell has lost the ability to replicate even in the presence of normally appropriate replicative signals.

"Spot" means the area taken up by a specific fluorescent signal in a FISH analysis image; spot size corresponds to the amount of probe hybridized to a telomere.

"Subtelomeric DNA" or "Subtelomeric region" means chromosomal DNA located immediately adjacent (100 to 500 bp but can be up to 1 kb) to the tandem telomeric repeats of the telomeric DNA and generally contains telomeric repeat sequences interspersed with imperfect telomeric repeat or other variable sequences.

"Subtelomeric region of an abnormal chromosome" means the chromosomal DNA immediately adjacent (100 to 500 bp but up to 1 kb) to a telomere of an abnormal chromosome, e.g., the region adjacent to a telomere from a diseased cell, such as those found in α-thalassaemia patients or formed by recombination-based chromosome truncation (Farr et al., 88 *PNAS* 7006, 1991).

"Telomeric DNA" or "Telomeric region" means the chromosomal DNA located on the ends of a chromosome consisting of a tandem repeat array of a short sequence. In humans, the telomere region is composed of 5'-TTAGGG-3' repeats and the corresponding complementary sequence. The telomeric regions of different organisms differ with respect to telomeric repeat sequence. The telomeric repeat sequence of telomeres from a variety of organisms, including human, *Tetrahymena,* fungi, and non-human mammals, are known. For instance, *Tetrahymena telomeres* consist of repeats of sequence 5'-TTGGGG-3', and the corresponding complementary sequences. Consequently, if one is using the present methodologies to determine telomere length of telomeres in a sample of human origin, one will employ a probe or primer distinct from that employed if the sample is, for example, of fungal origin. For convenience, human telomeric region and human telomeric repeat sequences are typically referred to herein for illustrative purposes. This illustrative use is not intended to limit the invention, and those of skill in the art will recognize that the present methods can be used to measure telomere length of telomeres from any organism.

"Terminal restriction fragment" or "TRF" means the length (or average length) of restriction fragments that are generated by complete digestion of the genomic DNA with one or more restriction enzyme(s) that do(es) not cleave nucleic acids composed entirely of tandem arrays of telomeric repeat sequences and that comprise both telomeric repeats and subtelomeric DNA.

"3' end of the telomere" means the single-tranded region of the telomere; in humans this region is located on the G-rich strand, and is composed of a 5'-(TTAGGG)$_n$ repeat sequence, where n is typically 9 to 35 (but n can be more than 35 or less than 9).

Primer Extension Based Methods for Measuring Telomere Length

The present invention provides methods for measuring telomere length. In one embodiment, the method comprises the steps of:

(a) covalently attaching an oligonucleotide linker to a telomere for which a measure of length is desired;

(b) contacting a primer comprising a sequence sufficiently complementary to said linker to hybridize specifically thereto under conditions such that said primer extends to form a primer extension product complementary to said telomere; and (c) correlating telomere length with primer extension product size, thereby providing a measure of telomere length.

In one embodiment, this method involves contacting the telomere with a linker under conditions in which the linker is ligated by the action of a DNA or RNA ligase that can "blunt-end" ligate together two single-stranded RNA or DNA molecules. This method can also be employed using a double-stranded linker. Alternatively, the linker can be attached nucleotide-by-nucleotide by a terminal transferase and specific dNTPs (dCTP, dTTP, dGTP or DATP, depending on the sequence to be added). Terminal transferase can add multiple monomers of a specified dNTP to the 3' end of the telomere; the added nucleotides can then serve as a primer annealing site.

An oligonucleotide complementary in sequence to the sequence of the linker is used as a primer in the replication step. This oligonucleotide is referred to as the "forward primer". In addition to the forward primer, a second primer can preferably be used. The telomere sequences are replicated or amplified, for example, by PCR amplification with a first primer specific for the linker sequence and a second primer specific for a subtelomeric region of the chromosome. The primers can be extended by any means that requires the presence of the telomeric region for primer extension to occur; preferred means are mediated by a template-dependent DNA or RNA polymerase, a template dependent DNA or RNA ligase, or a combination of the two.

Telomeric nucleic acids in a sample are covalently bound to a linker, and a primer complementary to the linker and/or a subtelomeric primer provide(s) a substrate for either DNA or RNA polymerase or DNA ligase to produce primer extension product(s) complementary to the telomeric region.

As noted above, if the primer extension reagent is a DNA polymerase, and a second primer is present, one has the requisite components for PCR, a process more fully described in U.S. Pat. Nos. 4,683,195; 4,683,202; and 4,965,188, provided the appropriate buffer and nucleoside triphosphates are present in the reaction mixture. Taq polymerase (available form Perkin-Elmer) is a preferred polymerase in PCR amplification, although other polymerases, especially thermostable polymerases, can be employed. Taq polymerase can misincorporate nucleotides in the primer extension. If misincorporation presents a problem, and typically, the misincorporation is at such a low frequency that no problem is encountered unless the amplification products are very long, then another polymerase with a lower frequency of misincorporation, i.e., Pfu, Pwo, or Vent can be employed, or a mixture of such polymerases, i.e., Taq polymerase/Vent DNA polymerase in a ratio range of 100:1 to 10:1, can be employed. The appropriate selection of a polymerase or a polymerase mixture can provide optimal extension of the primer extension product.

Once a primer extension product has formed, one can disassociate or denature (typically by heat denaturation, but other methods, i.e., enzyme or chemical mediated processes, such as helicase mediated denaturation, can be used) the primer extension product from the telomeric region. If additional primer and primer extension reagent is present in the sample, then a new primer/telomere complex can form, leading to the production of additional primer extension products. One can repeat the process of primer extension and denaturation several to many times, as desired. Typically, primer extension and denaturation of extended primer/ telomere complexes will be performed at least 5, 10, 15, 20, to 30 or more times. Moreover, if a second primer complementary to the subtelomeric region of the extended primer is present in the reaction mixture, one can increase the replication products (both extended primer and the complementary extended sequence) dramatically, because the two primers mediate PCR amplification of the telomere.

The PCR cycles are composed of cycle times and temperatures that can vary widely, depending upon the sample, detection format, and application. Typically, long PCR reaction conditions are employed. The simplest PCR cycle comprises a duplex nucleic acid denaturation step followed by a primer annealing and extension step. The denaturation step typically involves heating at any of a relatively wide range of temperatures for an amount of time sufficient to denature but not damage the DNA. In similar fashion, the time and temperature of the primer annealing step depend on the reaction buffer and primer sequence, concentration, and composition, as well as the specificity required by the practitioner. The time and temperature of the primer extension step depend upon the type of DNA polymerase or ligase employed. Those of skill in the art will recognize and understand that the present invention is not limited by the times, temperatures, and reaction condition variations in buffer and other reaction components that can be employed.

The second primer used in this embodiment is a primer comprising sequences complementary to the subtelomeric region and is designated the "subtelomeric primer." FIG. 1 illustrates this method, showing Pi as the subtelomeric primer, P2 as the forward primer, and the zigzag line indicates the junction between the subtelomeric region and the telomere (the figure is not drawn to scale). In this Figure, the telomere is a human telomere and so comprises the human telomeric repeat 5'-TTAGGG-3' and complementary repeat sequences. The region depicted by heavy right angled slashed lines in FIG. 1 represents the subtelomeric region complementary to the subtelomeric primer. Preferably, the subtelomeric primer does not comprise a telomeric repeat sequence and so is a non-telomeric repeat sequence of the subtelomeric region. Preferably, the subtelomeric primer anneals to the subtelomeric region within 50 base pairs of the junction with the telomeric region. Extension of these primers in multiple cycles of primer annealing and extension amplifies the telomeric region by producing multiple replicates of the same.

If the primer extension product is generated by PCR, then, as noted above, one also employs a primer specific for the subtelomeric region. This primer is a site specific and, preferably, a chromosome specific primer. The subtelomeric primer is complementary to a sequence in the subtelomeric region that is present in at least one chromosome, but optionally present in two or more, up to and including all chromosomes, of the cell or cell population of interest. Subtelomeric regions of many different chromosomes are known in the art. Additional subtelomeric regions of normal and abnormal chromosomes can be determined using cloning and sequencing procedures known in the art.

Primers specific for a subtelomeric region of a normal chromosome include novel primers based on the heretofore unpublished TelBam 8 probe sequence, specific for chromosome 7q, such as TEL8-1, 5'-TGCAATTATTTTACTATCTGTTATCGG-3' (SEQ. ID NO.:1); and TEL8-2, 5'-TGACCTGTTTTAAAGAGTATGCTCAG-3' (SEQ. ID NO.:2). Nucleic acids comprising all or portions of the TelBam 8 probe sequence can be cloned as described in Brown et al., 63 Cell 119, 1990.

Other illustrative subtelomeric primers include XpJCTN, 5'-CCCTCTGAAAGTGGACCWATCAG-3' (SEQ. ID NO.:3), where XpJCTN is a mixture of two primers, in one of which W is A and in the other of which W is T; 40BPXpJCTN, 5'-CTTTTATTCTCTAATCTGCTCCC-3' (SEQ. ID NO.:4); 400BPXpJCTN, 5'-TAGGGGTTGTCTCAGGGTCCTA-3' (SEQ. ID NO.:5); REV40BPXpJCTN, 5'-GGGAGCAGATTAGAGAATAAAAG-3'(SEQ. ID NO.:6); and revXpJCTN, 5'-CTGATWGGTCCACTTTCAGAGGG-3'(SEQ. ID NO.:7), which are based on sequences in the pseudo-autosomal region of the X and Y chromosomes (Baird et al. 14 *The EMBO Journal* 5433, 1995)

By attaching a linker to the 3' end(s) of the chromosome (s), and using a forward primer specific for the linker and a primer complementary to the subtelomeric region of a chromosome (e.g., a primer incorporating a subtelomeric sequence, such as the sequence of the TelBam 8 probe or the pseudo-autosomal region of chromosomes X and Y), PCR amplification can generate multiple copies or replicates of the telomeric region, which can in turn be used to measure telomere length. The PCR primer extension products are, for example, separated by size on a gel. If the amplification products have been labeled, i.e., by incorporation of a labeled nucleotide or hybridization to a labeled probe, then one can use size standards to determine telomere length. Direct incorporation of labeled nucleotides into the amplification products allows for elimination of the steps comprising denaturing the DNA in the gel, neutralizing the gel, drying the gel, hybridizing a probe to the gel, removing unbound probe from the gel, and exposing the gel, typically undertaken in conventional probe-based methods. Relative to conventional methods, which can require about a week to complete, the PCR-based method for measuring telomere length is quick, accurate, sensitive, and requires significantly less sample to perform.

In a preferred embodiment of this method, the linker is a double-stranded oligonucleotide, and the telomeric DNA is treated prior to linker attachment to remove or fill in single-stranded regions. In this embodiment, as exemplified in Example 4, the DNA is treated with a nuclease (i.e., Bal31, Mung bean, or other nuclease) and/or DNA polymerase, such as T4 or Pfu (these polymerases possess 3' to 5' exonuclease activity in combination with their 5' to 3' polymerase activity), to generate blunt-ended, double-stranded telomere ends prior to ligation of the double-stranded linker.

While those of skill in the art will recognize that any double-stranded linker can be used, so long as the linker sequence differs from the telomeric repeat sequence, a particularly preferred double-stranded linker is composed of complementary single-stranded oligonucleotides SLIC-II and aSLIC (see Edwards et al., 19 *Nucl. Acids Res.* 5227, 1991), shown below.

5'-GGAATTCTGGTCGACGGATCCTGA-3' SLIC-II (SEQ. ID NO.:8)
3'-CCTTAAGACCAGCTGCCTAGGACT-5' aSLIC (SEQ. ID NO.:9)

The 5' end of the SLIC-II oligonucleotide can be constructed so as to terminate with a 5'-phosphate, whereas the 3' end of this oligonucleotide can be constructed with a terminal 2',3'-dideoxyadenosine group to prevent the linker from ligating to another linker. Likewise, the complementary aSLIC oligonucleotide can be constructed so that the 3' end terminates with a 2'3'-dideoxycytidine to prevent ligation to another linker. A double-stranded oligonucleotide formed by hybridization of SLIC-II to aSLIC so constructed cannot self-ligate.

The double-stranded oligonucleotide linker formed by SLIC-II hybridizing to aSLIC also contains restriction sites to facilitate cloning or other applications. This double-stranded oligonucleotide linker can be ligated to the 3' end of the blunted telomere using a ligase (i.e., T4 DNA ligase or other ligase). A primer complementary to SLIC-II, such as aSLIC, 5'-CCGTCGACCAGAATTCC-3' (SEQ. ID NO.:10) or 5'-CAGGATCCGTCGACCAG-3'(SEQ. ID NO.:11), can be used to generate the desired primer extension product. As noted above, the use of a second, subtelomeric primer for extension provides a means for PCR amplification of the telomeric region. Separation of the PCR amplified primer extension products by size on a gel and visualization of the products, for comparison to a standard(s) of known length (s), provides the length of the telomere DNA in the sample.

While the PCR based embodiments of the present invention are quite useful, the present method can be practiced using any method of primer extension to provide target amplification or with a method that provides for signal amplification or both, as described below. Moreover, target amplification can be achieved by means other than PCR. These methods include the ligase chain reaction (Barany, 88 *Proc. Natl. Acad. Sci. U.S.A.* 189, 1991), nucleic acid sequence-based amplification (Compton, 350 *Nature* 91, 1991), self-sustained sequence replication (Guatelli et al., 87 *Proc. Natl. Acad. Sci. U.S.A.* 1874, 1990), and strand displacement amplification (Walker et al., 89 *Proc. Natl. Acad. Sci. U.S.A.* 392, 1992). While PCR and other amplification methods provide for exponential accumulation of primer extension products, even linear accumulation of primer extension products can provide useful results. Thus, one can use a single primer and merely make many copies of the telomeric region from this one primer, as described more fully below.

This invention provides a method to measure telomere length using linear amplification. This method exploits the fact that the human telomeric repeat sequence lacks guanidine residues in the C-rich strand; however, this method is generically applicable to telomeres of any origin that comprise repeat sequences that lack one or more nucleotides. In this embodiment, a primer complementary to the covalently bound linker is added to the genomic telomere DNA in the presence of only three (for human telomeres, DATP, dTTP, and dCTP) of the four nucleoside triphosphates. These three dNTPs form the complement to the G-rich stand of a human telomere. Usually, the primer or at least one of the triphosphates is labeled with a detectable label, e.g. a radioisotope or a fluorescent molecule, which label is retained upon incorporation into the primer extension product.

The primer is extended by means of a primer extension reagent, e.g., a DNA polymerase such as the Klenow fragment of DNA polymerase I, T7 DNA polymerase, or Taq DNA polymerase or the Stoffel fragment thereof. Exclusion of dGTP results in termination of the primer extension at the first C nucleotide of the chromosome. Thus, sequences complementary to the primer located outside the telomeric and/or subtelomeric region would not serve as templates for primer extension products due to the lack of dGTP. Denaturation of the primer extension product from the telomeric DNA followed by repeated cycles of primer extension results in the generation of multiple copies or replicates of one strand, for human chromosomes, the G-rich strands, of the telomeric region. For many purposes, a simple measure of the label incorporated suffices to quantitate telomere length, although one can also measure the length directly by gel electrophoresis and comparison to standards of known length.

In a preferred embodiment, the annealed primer is extended in the presence of a mixture of dideoxy GTP (ddGTP), dCTP, DATP, and dTTP by a polymerase (for human telomeres). The method differs from the previous embodiment in that, instead of leaving one or more nucleotides out of the reaction mixture, one uses a chain-terminating nucleotide(s) in place of the otherwise missing nucleotide(s). Polymerization proceeds until the polymerase encounters the first cytosine residue (for humans) in the subtelomeric region. The enzyme will then incorporate the ddGTP nucleotide and further extension will be terminated due to the presence of the ddGTP. The primer extension reaction can repeated as many times as desired. The length of the extended DNA can be determined by gel electrophoresis and comparison to standards, as described above. In addition, the amount of DNA synthesized can be determined by measuring the label incorporated into the primer extension products or the amount of probe hybridized to the primer extension products, which will be directly proportional to telomere length. While the manner of determining primer extension size may vary depending upon the method of analysis selected, any of the methods described can be used.

In another embodiment of this method, linear extension products generated using a subtelomeric primer serve to provide a measure of telomere length. This embodiment eliminates the need for ligating or otherwise covalently attaching a linker to the 3' end of the telomere. As above, this embodiment is ideally suited for linear amplification resulting in multiple copies of the telomeric region.

If the subtelomeric primer selected is not specific or unique to the subtelomeric region, then the primer extension products generated from the subtelomeric region can be distinguished from those generated from an internal chromosomal region by hybridizing with a probe that is specific to a telomeric region or a region immediately adjacent to the telomeric repeat sequences. Alternatively, if the subtelomeric primer hybridizes to multiple sites within the subtelomeric region, then one can hybridize a primer specific to a region immediately adjacent to the telomeric repeat sequences, and this second subtelomeric primer can be annealed to the first primer extension products and extended with DNA polymerase and the size of the second primer extension products determined as described above to provide a measure of the subtelomeric length in the first primer extension products.

Another embodiment of the invention involving the use of chain-terminating synthetic nucleotide(s), such as a dideoxynucleotide, eliminates the need to attach a linker covalently to the 3' end of the telomere. This method comprises the steps of:

(a) contacting double-stranded chromosomal DNA in a sample with a primer having a sequence sufficiently complementary to the 3' end of a telomere to hybridize therewith in the presence of a mixture of nucleotides and a dideoxynucleotide under conditions such that said primer extends to form a primer extension product terminating with said dideoxynucleotide; and (b) correlating telomere length with primer extension product size to provide a measure of telomere length.

As noted above, this method can be used as a variation of the linker-based method, where the primer is complementary to a linker added to the 3' end of the telomere, but in a preferred embodiment, no linker is required. In this embodiment, an oligonucleotide sequence complementary to the 3' single-stranded region of the telomere, i.e., 5'-(CCCTAA)$_4$-3' (SEQ. ID NO.:12), is annealed to the telomeric DNA termini. The annealed primer is extended in the presence of a mixture of dideoxy GTP (ddGTP), dCTP, DATP, and dTTP by a polymerase (for human telomeres). In a preferred embodiment, one of the nucleotides is labeled (typically, in any method involving incorporation of a labeled nucleotide, especially a radioactively labeled nucleotide, only a small fraction of the total nucleotide is labeled, and so the labeled nucleotide is referred to as a "tracer"). The polymerization will proceed until the polymerase encounters the first cytosine residue in the subtelomeric region, as described above. The DNA is then denatured and separated by size on a gel. Incorporation of a labeled nucleotide provides for easy identification of the length of the extension product on a gel and direct correlation of telomere length from signal intensity. One can, however, also use a labeled probe to detect primer extension products.

In a more preferred embodiment of this method, the genomic DNA is fragmented with a restriction enzyme that cuts DNA, but not telomeric DNA, frequently, i.e., for human chromosomes, HinfI or any other restriction enzymes with relatively short recognition sequences, and subsequently treated with a polymerase (i.e., DNA polymerase I or the Klenow fragment thereof, Taq polymerase or the Stoffel fragment thereof) in the presence of ddGTP, dCTP, dATP and dTTP, prior to addition of the primer. This treatment fills in nicks and gaps in the genomic DNA and blocks any potential priming sites in the genomic DNA with a ddGTP chain terminator. Pretreatment of the DNA to fill in gaps and nicks can result in increased sensitivity and decreased background signal. An oligonucleotide primer with a sequence complementary to the 3' single strand region of the telomere is then added and annealed to the telomeric DNA termini and extended as discussed above. As before, telomere length is determined by correlation to the size of the primer extension products.

The foregoing methods involve the use of a primer and the detection of primer extension products to measure telomere length. The following two sections describe methods using a probe to measure telomere length.

Probe Based Methods for Measuring Telomere Length

In another aspect of the invention, labeled probes are employed to measure telomere length. This method comprises the steps of:

(a) contacting denatured chromosomal DNA with a labeled probe having a sequence complementary to a telomere repeat sequence under conditions such that said probe hybridizes specifically to telomeric DNA;

(b) measuring amount of bound probe; and (c) correlating said amount of bound probe measured with telomere length.

In these probe-based methods, the probe is added in excess, so that all or substantially all of the telomeric repeats in the telomere are hybridized to the probe. Typically, the correlation step involves the use of standards of known length or the use of conversion factors to convert the amount of bound probe to a measure of telomere length.

This aspect of the invention provides a method for measuring telomere length in which an oligonucleotide probe is hybridized to telomere repeat sequences. The amount of probe hybridized is determined and then correlated to provide a measure of telomere length. This method can be practiced without the gel based size separation step used in other methods. Thus, this aspect of the invention provides a rapid, high through-put method for measuring telomere length.

In a preferred embodiment, this method involves preparing DNA extracts of cells, incubating the extract with an oligonucleotide probe complementary to telomere repeat sequences, and determining amount of probe bound as a measure of telomere length. For convenience, the cells can be grown in a 24, 48, or 96-well microtiter plate.

To practice the method, the cells from each well are collected and the DNA isolated by standard DNA extraction procedures. The DNA extract solution can be passed through a DNA-binding filter, such as nitrocellulose or Biodyne B membrane, to remove other potentially interfering substances. The filter is then contacted with a labeled oligonucleotide probe having a sequence complementary to telomere repeat sequences. After unbound probe is removed, the amount of probe bound to the filter is then quantified, and the amount of probe bound provides a measure of telomere length. This method, called the dot-blot method, is exemplified in Example 1 below. As with other embodiments, standards of known telomere length can be employed to help correlate the signal from bound probe with telomere length. In a preferred embodiment, this method is carried out in a 24, 48, or 96-well plate and is automated. Preferably, Pall SILENT MONITOR™ 96-well test plates, having 0.4 μM Biodyne B membrane located at the bottom of each well, are used.

In another embodiment, the invention provides a method of measuring telomere length in which the genomic (chromosomal) DNA is bound to a solid phase using a modified dot-blot method called the slot-blot. This aspect of the invention is illustrated in Example 2. The slot-blot is described for a distinct application in Kafatos et al., 7 Nucl. Acid Res. 1541, 1979, and has been used to determine the relative concentrations of nucleic acids in a mixture. A distinct DNA to membrane cross-linking step and unique filtration apparatus distinguish this method from the dot-blot method described above. In this embodiment of the invention, samples of nucleic acid (i.e., genomic DNA) are spotted on and cross-linked to a nitrocellulose filter (e.g., Schleicher & Schuell nitrocellulose filter) using UV irradiation, and the nucleic acid on the filter is hybridized with a labeled oligonucleotide probe. Typically, the genomic DNA is sheared or cleaved into smaller fragments prior to binding to the solid phase. The genomic DNA is cleaved or sheared enzymatically or mechanically, i.e., with restriction endonucleases, sonication, or other methods known in the art. In a preferred method, the cleaved DNA is probed with a riboprobe. The amount of probe hybridized to the nucleic acid in each of the slots is quantitated, and the quantitated amount is correlated with telomere length, e.g., by comparing to a standard.

In another embodiment, one measures the loss of or decrease in bound probe observed after treatment of the genomic DNA with a known amount of exonuclease that degrades DNA specifically from the ends of the chromosome to measure telomere length. A preferred exonuclease is Bal31, an exonuclease that digests single- or double-stranded DNA specifically from the end of a DNA, such as the end of a telomere. The rate of Bal31 digestion is about 50 bp/min. Thus, when chromosomal DNA is digested with Bal31, DNA internal to the telomeres is digested last while telomeric DNA is digested first. The method can be conveniently carried out by spotting Bal31 enzyme (i.e., serial dilutions) on a DNA binding membrane, i.e., nitrocellulose, located on the bottom of each well of a plate, binding genomic DNA to the membrane, incubating under conditions where the nuclease enzyme is active for a specific period of time, denaturing the enzyme and DNA, and hybridizing the remaining DNA to a telomeric probe, i.e., for human DNA, a probe comprising 5'-TTAGGG-3' repeats, under hybridizing conditions. The amount of probe hybridization, which should decrease with increasing Bal31 concentration or reaction time, can again be used to determine the telomere length. Preferably, this method is carried out in a multi-well, i.e., 96-well, format and, more preferably, is automated. If desired, telomeres of known length or cells comprising telomeres of known length can be used as standards.

Telomere Length Measurement in Whole-Cells

The methods of the invention can be applied to whole cells, as well as cell extracts. In one embodiment, whole cells are attached to a solid support or surface; the cells are permeabilized; the cellular DNA is denatured; and a labeled telomere probe (or a mixture of labeled probes) is added and hybridized to the telomeric repeats in the denatured DNA. In preferred embodiments, a fluorescein tag and "anti-fade" agents, as described below, are used, and the results of this "fluorescence in situ hybridization" (FISH) are analyzed using confocal microscopy. See Trask et al., 91 *Proc. Natl. Acad. Sci. U.S.A.* 9857, 1979, incorporated herein by reference.

In a preferred embodiment, this method is used to measure telomere lengths of chromosomes in a metaphase spread. Chromosomes are stained or labeled with a chromosomal dye (e.g., DAPI/DA); the slides are preferably prepared using antifade mounting medium (e.g. 9:1 glycerol:PBS containing 0.1% p-phenylenediamine buffered to pH 8.0 with 0.5M carbonate/bicarbonate buffer). The fluorescent signal is preferably amplified. The results can be analyzed with an image generator in conjunction with an inverted fluorescence microscope.

FISH analysis of cells or metaphase spreads of cells can be used for a variety of purposes: to determine average relative telomere lengths in cells in a tissue sample; to determine the longest telomere length in cells in a sample; to detect the presence of certain types of cells, i.e. certain stem cells can be identified by their long telomeres; to determine the size distribution of telomere lengths in a sample; to determine changes in telomere length in a cell population over time or after treatment with an agent or exposure to certain conditions; and to detect different cell types within a tissue, i.e., cancer cells can be identified by their having telomeres of a different length than that observed in normal cells, such as cells adjacent to tumor cells.

Quantitative FISH analysis with confocal microscopy using signal integration also allows one to obtain an objective measure of the distribution of telomere lengths on different chromosomes and to identify chromosomes which have lost a critical amount of telomeric DNA, indicative of the presence of aberrant cells. The method requires only relatively small samples and allows for direct measurement of telomere length on a chromosome-by-chromosome and cell-by-cell basis. The intensity of signal from bound probe per chromosome or cell is proportional to the number of telomeric repeats, and thus to the telomere length. The method also provides a means to investigate telomere heterogeneity in cell or tissue samples; such information can be especially useful when combined with information regarding the presence and amount of telomerase activity in the sample (Harley et al. PCT Pub. No. 95/13381, published May 18, 1995; Harley et al. U.S. application Ser. No. 08/631,554, filed Apr. 12, 1996; and Harley et al. U.S. application Ser. No. 08/632,662, filed Apr. 15, 1996).

Many variations of in situ hybridization can be applied in the methods of the invention. For example, a variation of the in situ hybridization detection method involves primed in situ labeling ("PRINS"; Koch, J., in "Nonradioactive in situ Hybridization Application Manual" (1992), Boehringer Mannheim, 31–33). This method involves the use of a primer but is discussed in this section for ease of understanding. Detection of telomere repeats by PRINS involves using an oligonucleotide primer specific for telomere repeats and chain elongation incorporating labeled nucleotides. In a typical protocol, a PRINS reaction mixture (10 $\mu$l) of 5% (v/v) glycerol; 10 mM Tris-HCl, pH 8.3; 100 mM KCl; 0.05% (w/v) Tween 20; 0.75 mM EGTA; 2.5 mM $MgCl_2$; 0.4 $\mu$M return primer; 200 $\mu$M DATP, dGTP, dCTP; 110 $\mu$M dTTP; 90 mM labeled dUTP is placed on a fixed, permeabilized sample, sealed with a coverslip, anchored with nail polish, overlayed with mineral oil, and incubated at 70° C. for 30 minutes to 3 hours. After completion of the PRINS, the sample is washed 3 times in wash buffer (0.6M NaCl and 0.06M sodium citrate (4×SSC); 0.05% Tween 20) heated to 70° C. for 2 minutes, and the signal observed as described above. To reduce the background signals that can arise from direct incorporation of fluorescent labels during primer extension, indirect detection using unlabeled dNTPs and unlabeled primers can be used and the product detected using a labeled probe.

In an additional preferred embodiment, the method allows one to determine cellular DNA content simultaneously with measuring telomere length. Cellular DNA content can indicate whether a cell is proliferating or senescent. If the cell is proliferating, the chromosomal DNA content can increase up to two-fold. Consequently, the signal intensity of the bound telomeric probe for a rapidly proliferating cell with short telomeres can be equal to or stronger than that of a non-dividing cell with longer telomeres. Thus, this method may be useful to normalize the measured signal intensity of the telomeric probe with respect to DNA content. The method comprises the steps of attaching cells or metaphase spreads to a support; denaturing the cellular DNA; contacting the chromosomal DNA with a labeled telomeric probe and a DNA specific dye; hybridizing the denatured DNA with the probe; and measuring the amount of probe hybridized and cellular DNA content simultaneously using flow cytometry. This method allows one to determine cell cycle position as well as telomere length. The intensity of signal from bound probe per chromosome or cell is proportional to the number of telomeric repeats, and thus to the telomere length. One advantage of this method is that cells can then be sorted, e.g., using a flow cytometer (Coulter EPICS ELITE fluorescence activated cell sorter (FACS)), based on telomere length. The instrument can be programmed to deflect the cells into specific tubes based upon telomere length.

As noted above, the invention provides for the measurement of the length of a telomere of an individual chromosome. Flow cytometry facilitates this analysis. A combination of fluorescent dyes (e.g., chromomycin A3, a major or minor groove binding dye with relative GC specificity, and bisbenzimide 33242, a groove binding dye with relative AT-specificity) in conjunction with a probe hybridized to the telomeric region, can be used to direct the flow cytometer to analyze and sort isolated metaphase chromosomes by telomere length. The chromosomes can be labeled to obtain a direct measure of the telomere length of an individual chromosome and subsequently sorted using a three-laser flow cytometer. The measurement is made by quantifying the fluorescent intensity for each individual chromosome using flow cytometry analysis. Alternatively, simultaneous three-color staining methods, in which the chromosomes are prepared, sorted, and subsequently hybridized in solution, can be applied to telomere length analysis of individual chromosomes.

The methods of the invention can be performed rapidly and provide increased sensitivity, efficiency, reliability and accuracy. Moreover, these methods for telomere length measurement can be employed in a high through-put and/or automated process format. These telomere length measurement methods can be used for diagnostic, prognostic, and research applications.

Applications

Telomere length measurement has useful application in medical diagnostics, prognostics, and therapeutics. Such applications include, but are not limited to: (I) determination of the proliferative lifespan of cells; (ii) identification and analysis of the effectiveness of agents capable of extending, maintaining, or reducing telomere length; (iii) diagnosis of disease or medical conditions characterized by a different telomere length in a patient relative to an individual not having the disease or particular medical condition; (iv) prognosis of disease or medical conditions as correlated to telomere length; and (v) identification of cells, cell types, or cell populations. In general, measurement of telomere length provides a powerful means to assess and monitor cellular lifespan for a variety of useful purposes.

The length of the telomeres of the chromosomes in a cell is indicative of the proliferative capacity of that cell, and so provides an indicator of the health of an individual or organism comprising such cells. Certain populations of cells may lose telomeres at a greater rate than the other cells within an individual. Rapid and/or extended proliferation of those cells may make that cell population age-limited or senescent, with negative impact on an individual relying on that cell population for health. The diagnostic procedures described herein can be used to indicate the potential life span of any cell type, as well as to follow telomere loss over time, so that revised estimates of life span can be made over time.

Telomere length measurement can be used to monitor the effectiveness of various therapeutics in expanding and/or reducing the proliferative lifespan of cells. In one example, cells treated with an oligonucleotide comprising telomeric sequences had a reduced rate of telomere loss and an increased proliferative capacity of about 10 population doublings. Conversely, the treatment of cells with AZT or other small organic molecule inhibitors of telomerase can increase telomere loss and reduce the proliferative capacity of the treated cells. Telomere length measurements facilitate the analysis of the efficacy of such agents on cells. See U.S. Pat. No. 5,489,508, issued Feb. 2, 1996.

Telomere length measurement can also be used to monitor the effectiveness of cancer chemotherapeutics during treatment. Telomere length measurement provides a means to determine the effectiveness of a telomerase inhibitor or other agent (i.e., a retinoid) that represses telomerase expression, because telomere length will decrease over time in dividing cancer cells in which there is inhibition of telomerase or telomerase expression. Measuring the telomere length of chromosomes in tumor cells can provide information regarding the proliferative capacity of such cells, both before and after administration of telomerase inhibitors or other treatments that affect telomere length. In a related application, one can measure the telomere length of telomeres in hematopoietic stem cells (HSCs) such as CD34+ cells, prior to use in bone marrow transplantation. The longer the telomeres, the more likely the cells will successfully engraft.

The methods of the invention are also generally useful in discovering agents that modulate telomere length. Cells can be treated with test agents (e.g., synthetic compounds, fermentation extracts, nucleic acid preparations, and other agents) during culture to determine the effect of such test agents on telomere length and telomere maintenance of specific chromosomes.

In diagnostic applications of the invention, telomere length measurement can detect a change in telomere length and/or the rate of telomere loss. A tissue can have a spectrum of cells of different proliferative capacity. Average telomere length for a tissue will be informative of the state of the tissue generally. Multiple measurements of telomere length over time can be used to determine the rate at which the telomere length changes over time.

In addition, telomere length measurement methods of the invention can be used to diagnose the presence of abnormal chromosomes. If one uses a primer specific for a known subtelomeric region of an abnormal chromosome, such as chromosome 6 from cells of α-thalassaemia patients, the primer based methods of the invention can be used to diagnose the disease states associated with such cells. The presence of primer extension products is indicative of the presence of the abnormal chromosome indicative of the disease state.

In prognostic applications of the invention, telomere length measurement can detect whether a cellular disease, such as cirrhosis of the liver or muscular dystrophy, has affected the proliferative capacity of the diseased tissue so as to impact the recuperative capacity of the patient. In other situations, such as those involving injury to a tissue, as in surgery, wounds, burns, and the like, the ability of cells, e.g., fibroblasts, to regenerate will be of interest, and telomere length, a function of proliferative capacity, provides such information. Similarly, in the case of bone loss, osteoarthritis, or other disease requiring reformation of bone, the renewal or proliferative capacity of osteoblasts and chondrocytes will be of interest, and again, telomere length provides an indicator of proliferative capacity. In addition to cellular diseases, diseases associated with aging can be diagnosed using the present methods. In these applications, telomere length provides an indicator of proliferative capacity, because the longer the telomere of a cell, the greater the potential replicative capacity that cell possesses.

A variety of diseases and disease states are amenable to diagnostic and prognostic evaluation by telomere length measurement. For example, there is a reduction in telomere length and replicative capacity in fibroblasts from patients with the accelerated aging syndrome Hutchison-Gilford progeria relative to age-matched normal individuals (Allsopp et al., 89 *Proc. Natl. Acad. Sci. U.S.A.* 10114, 1992). Accelerated telomeric loss is also associated with immunosenescence, such as that occurring prematurely in lymphocytes of individuals with Down's Syndrome (DS). DS patients show many features of premature aging, and lymphocytes from DS patients lose telomeres at three times the rate of age-matched controls (Vaziri et al., 52 *Am. J. Hum. Genet.* 661, 1993). Accelerated cellular turnover and concomitant telomere loss per cell division correlate with the premature aging phenotype, and telomere loss or short telomeres in immune cells is a biomarker of immunosenescence. Any disease associated with a higher rate of cell turnover or division is amenable to diagnosis and prognosis with the present invention.

For example, atherosclerosis in part results from a higher rate of cell turnover in the intimal and medial tissue in areas of atherosclerotic plaque relative to the surrounding normal tissue. Cells derived from these regions of atherosclerotic plaque undergo more cellular divisions than cells from plaque-free areas, in effect rendering the cells in plaque areas older and nearer to the end of their maximum replicative lifespan. Telomere length serves as a biomarker of cell turnover in tissues involved in atherosclerosis. In general, telomere loss in intimal and medial tissue underlying an atherosclerotic plaque is greater than that in plaque-free regions.

Formation of atherosclerotic plaques occurs more often in the iliac artery than in the iliac vein, and as expected, the decrease in mean TRF length in one test was shown to be significantly greater, over the age range, 20–60 years, for iliac arteries (–100 by/yr, P=0.01) than for iliac veins (47 bp/yr, P=0.14). See U.S. Pat. No. 5,489,508, issued Feb. 2, 1996. This decrease in mean TRF for plaque regions versus plaque-free regions of medial tissue from the same blood vessel is consistent with augmented cell turnover of tissue associated with atherosclerotic plaques. These results indicate that telomere length is a biomarker for cell turnover and proliferative capacity in tissues associated with cardiovascular disease, including cells of intimal and medial tissues.

Telomere length can be used not only as a biomarker for a disease condition but also as a prognostic indicator of disease stage. For example, in one study, telomere length measurements of CD28–CD8+ cells of HIV-infected subjects had significantly shorter TRF lengths than those of uninfected controls. In addition, the telomere length measurements of the lymphocyte subset of CD28–CD8+ cells compared to CD28+CD8+ cells in HIV-infected individuals for all subjects studied were consistently shorter. In fact, the mean TRF lengths of CD28−CD8+ cells of the HIV-infected subjects (5–7 kb) were similar to those observed for centenarians and for senescent T-cell cultures. Because loss of telomeric DNA is a marker of cell division, telomere shortening in CD8+ cells can be attributed to extensive cell division or turnover. Therefore, telomere shortening in the CD8+ cells can be ascribed to immune exhaustion that results from chronic-immune system activation and as such can be an indicator of HIV disease progression. Thus, telomere length in all cells such as CD8+ cells, CD4+ cells, and other cells of the immune system can be used for prognosis of the course of HIV infection or AIDS.

After a disease is diagnosed, telomere length measurement can be used to determine whether the disease is at an early or late stage of disease progression. For leukemia, telomere length is indicative of the time since disease onset and the relative rate of abnormal cell proliferation. Leukemic cells that have been dividing at increased rates for long periods of time have shorter telomeres than normal bone marrow cells. There is a progressive decrease in mean TRF length in blood and bone marrow leukocytes during the course of chronic lymphoid leukemia (CLL): the average TRF lengths in one study of CLL patients were: normal individuals (controls) 10.0–16.0 kb; early-stage CLL, 7.9 kb; and late stage CLL, 4.4 kb (Counter et al., 85 *Blood* 2315, 1995).

In chronic myeloid leukemia (CML) patients, there is a wide variation in TRF of bone marrow cells, i.e., the TRF is 2.8–12.8 kb. In one study of 44 CML patients, nine had a mean TRF length within the age-matched normal range. The remainder of the patients had short telomeres (average 5.6 kb) as compared to those of age-matched normal peripheral blood mononuclear cells. Those patients with shorter TRF lengths at the time of diagnosis experienced a shorter interval until blast crisis and responded less well to treatment than did patients with normal TRF. Telomere length depends upon the number of cell divisions and so, as illustrated in chronic CML patients, represents a new marker of disease state. CML patients having leukocytes with normal TRFs may be at an early stage of the disease and thus respond better to therapy.

In a similar fashion, the mean TRF was much shorter in the leukocytes of acute myeloid leukemia (AML) patients than in control leukocytes of bone marrow and peripheral blood from normal individuals. In addition, blast cells from seven AML patients had shorter telomeres than blood mononuclear cells isolated during remission (Yamada et al., 95 *J. Clin. Invest.* 1117, 1995). Thus, the presence of leukocytes (or other cells) with short TRF length is indicative of late stage or acute phase disease in these leukemias.

Telomere length measurement can also be used to diagnose fertility problems. In one study, telomere length was measured in sperm cells from both fertile and infertile males. Sperm cells from certain infertile males had significantly shorter telomeres than did sperm cells from the fertile males.

The methods of the invention have application in determining the proliferative capacity of a tissue as well as individual cells or cell types within a tissue. Many tissues regenerate from only a small number of stem cells. With in situ hybridization, one can identify and quantitate telomere length in such stem cells on an individual as well as collective basis. These methods allow one to determine telomere length on a chromosome-by-chromosome basis and to evaluate interchromosomal variance of telomere length. These measurements are made by quantitating the fluorescent intensity of bound probe for each individual cell nucleus or chromosome using confocal microscopy or flow cytometry analysis. Flow cytometry provides the added benefit of allowing the sorting of cells or chromosomes based on telomere length and cell type or chromosome identity (i.e., X chromosome separated from the Y and all other chromosomes). These sorted cells or chromosomes can then used as desired, i.e., for manipulation and/or subsequent therapeutic reintroduction into cell or, individual. These and other applications of the invention are further elaborated in the Examples below.

EXAMPLES

The following examples describe specific aspects of the invention to illustrate the invention and to provide a description of the methods for those of skill in the art. The examples should not be construed as limiting the invention, as the examples merely provide specific methodology useful in understanding and practicing the invention.

EXAMPLE 1

Dot-Blot Method for Measuring Telomere Length

This example describes a dot-blot method for measuring telomere length. Telomere length is determined by correlating the signal intensity of probe bound to the telomere region to telomere length. To facilitate understanding of the method, a number of different DNA preparation steps that can be used in the process are described. In addition, although solution compositions are provided, those of skill in the art will recognize that variations of these solutions can readily be made by appropriately modifying the concentrations of the various components in, as well as the composition of, the solution.

Two six-well plates of 293 cells seeded at 100,000 cells/well and one six-well plate of 293 seeded cells at 75,000 cells/well were washed twice with cold phosphate buffered saline solution (1×PBS is composed of 10 mM $K_3PO_4$ and 150 mM NaCl) to remove residual growth media. Cell membranes were lysed by adding 1.5 ml of extraction buffer (extraction buffer is 10 mM Tris, pH 8.0, 0.1M ethylenediaminotetraacetic acid (EDTA), pH 8.0, 0.1M NaCl, 0.5% sodium dodecyl sulfate (SDS), and 100 μg/ml proteinase K) to each well and incubating the samples at 50° C. for 3–16 hours; an additional aliquot (15 μl) of 10 mg/ml proteinase K was typically added after 1 hour.

After this incubation, the cellular RNA in the sample was degraded by adding 15 μl of 500 μg/ml DNase-free RNase to each well and incubating the samples for an additional hour at 37° C. The lysed cell extracts (referred to below as "DNA stock solutions") were then removed from the wells and transferred to tubes. The tubes were then heated at 65° C. for 10–20 minutes (at this point, the solutions can be snap frozen for later use). Alternate or additional DNA preparation steps can be used, e.g., enzymatic digestion (i.e., with proteolytic, RNase, or restriction enzymes), phenol extraction, and/or ethanol (EtOH) precipitation.

To demonstrate linearity of signal intensity to DNA concentration, aliquots of the DNA stock solutions, 150 μl, 75 μl, 37.5 μl, and 18.75 μl, were transferred from the tubes and spotted into individual wells of 96-well plates (Costar). The DNA was denatured in a solution of 0.4M NaOH and 10 mM EDTA, and the contents were transferred to 96-well filter plates. The filters were rinsed with 160 μl of 0.4M NaOH, vacuum filtered, rinsed with a solution of 0.3M NaCl and 0.03M sodium citrate (2×SSC) to remove the denaturing solution, and dried.

$^{32}$P-labeled riboprobe was prepared by combining in a sterile Eppendorf™ tube 50 μl of 5×transcription buffer (purchased from Stratagene), 10 μl of HindIII-digested pBL-Rep4 (1 μg/μl, purchased from Stratagene), 10 μl of 10 mM rATP, 10 μl of 10 mM rCTP, 10 μl of 10 mM rGTP, 10 μl of 0.75M dithiothreitol (DTT, purchased from Stratagene), 50 μl of $^{32}$P-UTP (0.25 mCi), 2 μl of T3 RNA Polymerase (purchased from Stratagene), and 98 μl of DEPC-treated water and incubating in a 37° C. water bath for 30 minutes. Plasmid pBLRep4 comprises 100 telomere repeat sequences (5'-TTAGGG-3') inserted into the EcoRl site of the plasmid pBluescriptIISK+ (Stratagene). After incubation, the tube was pulse spun in a Pico Fuge™ (Stratagene) and then 10 μl of RNase free DNase I (Boehringer Mannheim) was added, followed by incubation at 37° C. for 15 minutes. To the resultant mixture was added 260 μl of phenol/chloroform/isoamyl alcohol (PCIA, 26:25:1 ratio); the solution was vortexed and then certrifuged in a Pico Fuge™ (Stratagene) for approximately 4 minutes. After centrifugation, the top aqueous layer is transferred into another sterile, Eppendorf tube into which is also added approximately 26 μl of 3M sodium acetate. The reaction is mixed and then approximately 650 μl of 200 proof ethanol is added with mixing. The probe is precipitated out by maintaining the temperature of the tube at –20° C. for at least 30 minutes. The tube is then centrifuged for 10 minutes in the Pico Fuge™ (Stratagene). The supernatant is discarded and the pellet is resuspended in 100 μl of 1×TE buffer (1×TE buffer is composed of 10 mM Tris and 1 mM EDTA). The total volume in the tube is then brought up to 1 ml with 1×TE buffer. The resuspended probe can be stored at –20° C. until used.

Figure 2:
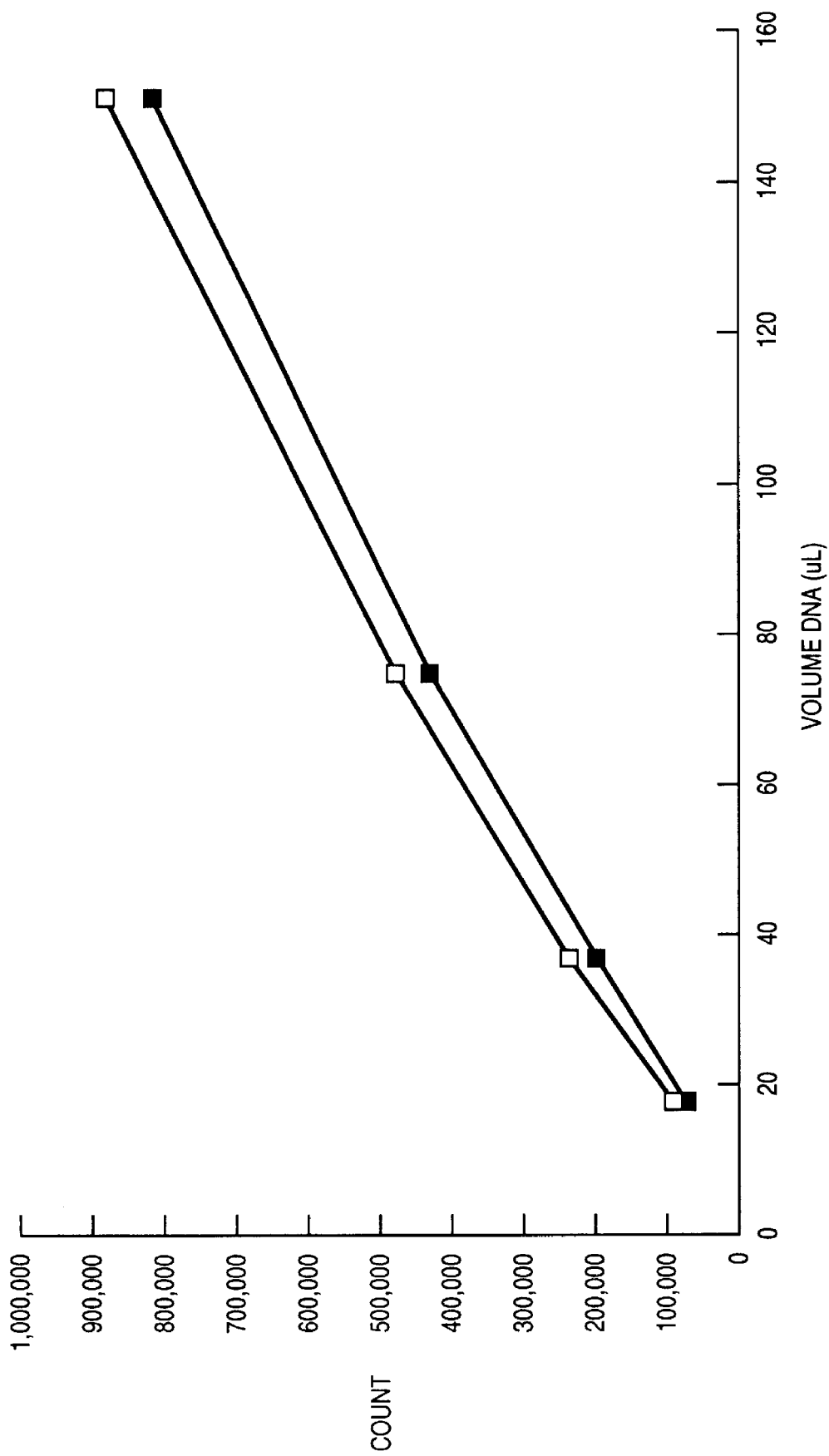
FIG. 2 graphically represents the results of probing different amounts of DNA with a telomere-specific probe using the modified dot-blot method (see Example 1). The graph shows that the signal increased with increased amount of telomeric DNA.

The DNA on the filters was then hybridized with 50 μl (50 μCi/μg DNA) of the $^{32}$P-UTP labeled riboprobe (comprising repeats of the sequence 5'-CCCTAA-3', as discussed above) in hybridization buffer (hybridization buffer is composed of 6×SSC, 1×Denhardt's solution, 20 mM sodium phosphate, pH 7.2, and 0.4% SDS) overnight at 65° C. The filters were washed four to five times in a wash solution composed of 1×SSC and 0.1% SDS and then exposed for at least 1 hour in a PhosphoImager cassette (Molecular Dynamics) and scanned. FIG. 2 shows the results presented graphically. The signal intensity increased with the amount of DNA, as demonstrated by this graph.

Known concentrations of DNA samples prepared from various cells (OVCAR 4, OVCAR 3, OVCAR 5, OVCAR 8, and SKOV-3) were analyzed with this method to measure differences in telomere length. As a comparison, the TRF lengths of these cells were also determined using a conventional method. Table 1 shows that signal intensity generally increased with increased TRF using the dot-blot method.

These data show, as predicted, that the TRF length also includes at least a portion of the length of the subtelomeric region. Using this method, one can calculate the length of the subtelomeric region included in the TRF length. This ability to distinguish subtelomeric length versus 5'-TTAGGG-3' telomeric repeat length has important implications in disease therapy and prognosis. Because the signal strength generated by this method is a more accurate indicator of replicative capacity than TRF length, this method can be used to determine which patients have a better prognosis and to determine the required duration of treatments, such as telomerase inhibition treatment. For example, as demonstrated in Table 1, OVCAR 8 comprises a shorter telomeric repeat region than OVCAR 4; however, the TRF of OVCAR 8 is greater, indicating that the TRF length for OVCAR 8 includes a greater portion of the subtelomeric region than that of OVCAR 4. Because the telomeric repeat length is indicative of the remaining proliferative capacity of the cell, a cancer patient with a tumor composed of cells like the OVCAR 8 cells would require a shorter period of treatment with a telomerase inhibitor than a patient with a tumor composed of cells such as OVCAR 4 cells, even though TRF length analysis would suggest otherwise. While the telomere length measurements undertaken in this example were for immortal cell lines, this method can also be used for mortal cell lines as a measure of replicative capacity.

EXAMPLE 2

Slot-Blot Method for Measuring Telomere Length

This example illustrates use of the slot-blot method for measuring telomere length. In this process, the DNA is cross-linked to a solid phase prior to hybridization with a probe.

About 1.5 μg of total genomic DNA from BJ cells (human foreskin fibroblast) and S2C cells (human skin fibroblast) at different PDL was completely digested overnight with a mixture of restriction enzymes EcoRI and HindIII. In addition, 1.25 μg of plasmid pBLRep4 was digested with restriction enzyme XbaI and used as a standard control. This amount of the plasmid is equivalent to 52.6 pmol of the DNA consisting of 5'-TTAGGG-3' repeats. The negative control, 1.5 μg of Lambda phage DNA, was digested with restriction enzymes Sau3A and HindIII and used to calculate the background signal.

The digested DNA was extracted with phenol/chloroform, precipitated with ethanol, and then resuspended in 100 μl of

TABLE 1

| Dot-Blot Method: Signal Intensity and TRF Length | | | | | |
|---|---|---|---|---|---|
| Sample | TRF(kb) | 2 μg DNA | 1 μg DNA | 0.5 μg DNA | 0.25 μg DNA | 0.125 μg DNA |
| OVCAR 5 | 2.39 | NT | 851742 | 439777 | 211908 | 104927 |
| OVCAR 3 | 3.55 | 2701170 | 1326068 | 608263 | 247371 | NT |
| OVCAR 4 | 4.89 | 3235960 | 1600895 | 688627 | 262075 | NT |
| OVCAR 8 | 7.51 | 2901921 | 1406973 | 633572 | 267539 | NT |
| SK-OV-3 | 10.69 | 5612527 | 2880505 | 1359104 | 512160 | NT |

NT - not tested.

For example, SK-OV-3 cells, which have the greatest TRF of the cells in these samples (10.69 kb), also exhibited the strongest signal using the dot-blot method at each concentration tested.

1×TE buffer (1×TE buffer is composed of 10 mM Tris and 1 mM EDTA). To this solution was added and mixed thoroughly 200 μl of 5×SSC.

A Schleicher & Schuell Minifold II™ apparatus was used to prepare the filters employed in the slot blot method. The blotting paper was wetted with 5×SSC, and each slot of the apparatus was rinsed with about 300 μl of 5×SSC. The digested DNA samples were then loaded into designated slots. To generate a standard curve on the blot, the digested plasmid pBLRep4 was diluted serially, and 0.009375 μg, 0.00625 μg, 0.003125 μg, and 0.0015625 μg were then loaded onto separate slots. All liquid was vacuum filtered through the blot; the DNA was retained on the blot. The blot was then removed and placed on a piece of 3 MM Whatman, paper (VWR) and air dried for 30 minutes.

The DNA was denatured by placing the blot on a stack of 3 MM paper soaked with a solution of 0.5N NaOH and 1.5M NaCl for 30 minutes. The DNA was then neutralized by placing the blot on 3 MM paper soaked with a solution of 0.5M Tris (pH 7.4) and 1.5M NaCl for 30 minutes. Following neutralization, the DNA was cross-linked to the blot with a UV STRATALINKER 1800™ device (Stratagene). Then, the DNA was incubated in 15 ml of prehybridization buffer (prehybridization buffer is composed of 5×SSC, 5×Denhardt's solution (1 g of Ficoll (Type 400, Pharmacia), 1 g of polyvinylpyrrolidone, 1 g of bovine serum albumin (Fraction V, Sigma, and sufficient water to make 100 ml), 0.02M phosphate (pH 6.5), 0.1 mg/ml salmon sperm DNA, 0.5% SDS, and 50% formamide) for 2 hours. This treatment was followed by hybridization of the DNA in 15 ml of prehybridization buffer containing $^{32}$P-labeled 5'-TTAGGGTTAGGGTTAGGG-3'(SEQ. ID NO.:13) probe (1 million cpm/ml), and incubation overnight at 37° C.

After probe hybridization, the blot was washed once with 500 ml of a solution composed of 1×SSC and 0.1% SDS for 10 minutes at room temperature, then washed twice with 500 ml of the same wash solution at 37° C. for 20 minutes, and then placed in a PhosphoImager™ detector overnight. The signal intensity of the hybridized probe was then analyzed.

Figure 3A:
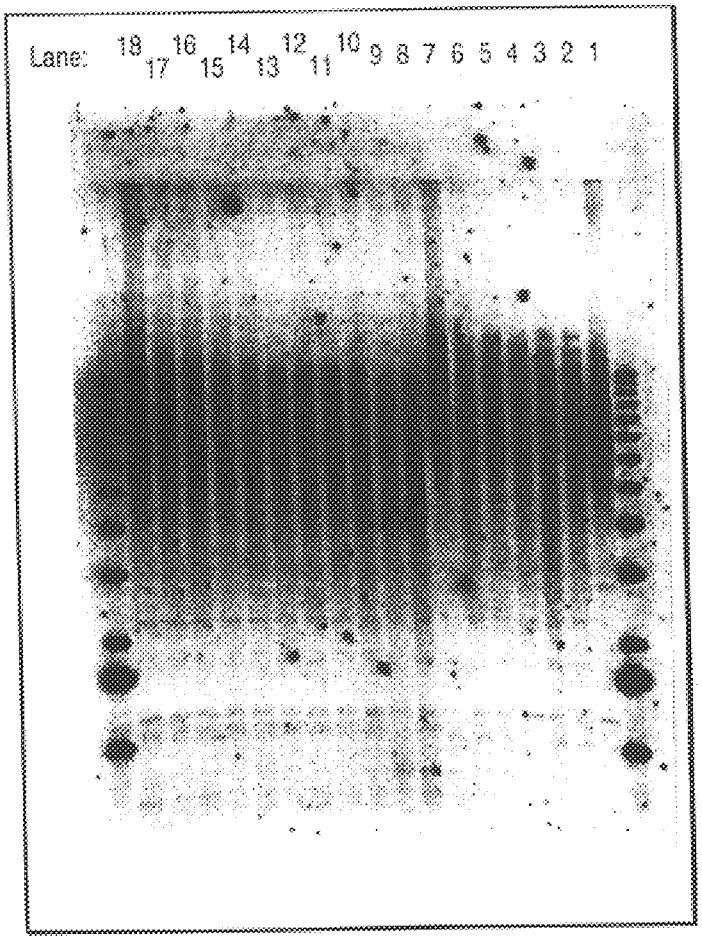

The signal intensity of probe hybridization in cells at different PDL was converted to a relative number that reflected the average length of telomeres according to the standard curve generated using the pBLRep4 control. The results, shown in Table 2, demonstrated generally a decrease in telomere length with increased PDL. The results correlate well with the corresponding TRF lengths and signal strength determined by conventional methods (see FIG. 3).

TABLE 2

Slot-Blot Method: PDL, Signal Intensity ("SI"), and Relative Signal Intensity ("RSI")

| BJ Cells | | | S2C Cells | | | Control pBLRep4 | |
|---|---|---|---|---|---|---|---|
| PDL | SI | RSI | PDL | SI | RSI | (pmol) | SI |
| 27.5 | 357338 | 100 | 30 | 286761 | 100 | 0.06576 | 76976 |
| 28.6 | 346486 | 97 | 39 | 258953 | 90 | 0.132 | 155074 |
| 41.2 | 280452 | 71 | 44 | 262724 | 91 | 0.263 | 285200 |
| 46.6 | 293800 | 81 | 47 | 209496 | 71 | 0.394 | 402212 |
| 57.2 | 270484 | 74 | 53 | 159030 | 52 | | |
| 69.2 | 219510 | 59 | 62 | 157456 | 52 | | |
| 72.2 | 230505 | 62 | 69.2 | 166010 | 54 | | |
| 73.5 | 194970 | 53 | 71.2 | 150172 | 49 | | |
| 80.0 | 219628 | 59 | 73.2 | 174636 | 58 | | |
| 88.2 | 119028 | 29 | | | | | |
| 91.4 | 113223 | 28 | | | | | |

The results in Table 2 show generally that bound probe signal intensity decreases with increased PDL. In addition, similar results were obtained for BJ cells and S2C cells, and signal intensity increased with increased amounts of the control, pBLRep4. The pBLRep4 plasmid results can be used to produce a standard curve generated by graphing known amounts of telomere repeat sequence versus the corresponding signal intensity determined using the slot-blot method. A standard curve generated using the data for pBLRep4 in Table 2 shows a linear increase in signal with increased amounts of pBLRep4.

EXAMPLE 3

Flow Cytometry for Telomere Length Quantitation

This example illustrates a method for measuring telomere length of the chromosomes of an individual cell. The method can be performed simultaneously with the analysis of cellular DNA content. This methodology also allows one to sort cells or chromosomes based on telomere length.

Growing cells are harvested by trypsinization and washed in PBS (phosphate-buffered saline), as per standard procedures. The washed cells are then fixed by adding freshly made, cold (4° C.) 3:1 100% anhydrous methanol:glacial acetic acid to the resuspended cell pellet with gentle mixing. Cells can be stored at 4° C. prior to analysis.

Alternatively, if one desires to measure the telomere length of a specific chromosome, the cells can be lysed to release intact nuclei, which are then fixed by incubation overnight in 2% paraformaldehyde (pH 7.0). Lysing the cells is accomplished by suspending the cells in 20 mM NaCl, 10 mM $MgCl_2$, 20 mM Tris (pH 7.2); incubating the cell suspension at 37° C. for 5 minutes; adding an equal volume of triton X-100 and mixing. For convenience, only analysis of intact cells, as opposed to nuclei, is described below. Those of skill in the art will recognize that this method is equally applicable to the analysis of telomeres of specific chromosomes.

Prior to hybridization, the cells are centrifuged and washed three times with PBS. Cells are then treated with RNase A for 20 minutes at 37° C. (100 μg/ml in PBS) followed by pepsin treatment (1 mg/ml, pH 2.0) for 5 minutes at 37° C.

The cells are centrifuged and then resuspended in hybridization buffer composed of 70% deionized formamide containing FITC-labeled PNA probe, sonicated salmon sperm DNA (or other commercially available reagent to prevent non-specific probe hybridization), and 10 mM Tris (pH 7.2), at room temperature for 2–8 hours. Because all cells fluoresce, a control experiment is conducted under the same conditions, except that the PNA probe is unlabeled to determine background fluorescence.

After the hybridization step, the cells are washed to remove unbound probe. The cells are washed three times in a solution composed of 70% formamide, 10 mM Tris (pH 7.2), and 0.05% triton X-100. The cells are then resuspended in PBS and analyzed on a flow cytometer.

Alternatively, a labeled DNA probe can be used in place of the PNA probe. If a DNA probe is used, the following procedure is implemented after fixing the cells. The DNA is denatured by adding 0.5 ml of a solution consisting of 70% deionized formamide and 2×SSC to the cell pellet (~1 million cells) and heating to 70° C. in a water bath for 2–5 minutes. The cells are then cooled on ice and centrifuged. The cell pellet is kept on ice until adding the probe to prevent renaturation of the DNA. The labeled DNA probe (i.e., biotin or digoxigenin) is suspended in 250 μL of hybridization solution (70% formamide, 2×SSC, 2×Denhardt's solution, 10% dextran sulfate, 50 mM Tris, pH 7.5), heated at 75°–80° C. for 10 minutes to denature the DNA, and cooled on ice. The cooled probe is added to the cell pellet and hybridized at 37° C. overnight. The cells are then washed in 50% formamide and 2×SSC at room temperature, collected by centrifugation, then resuspended in a solution containing streptavidin-FITC or a FITC-labeled anti-digoxigenin antibody. The resultant mixture is incubated at room temperature for one hour and the cells are collected by centrifugation and washed thoroughly. A control can be performed with steptavidin lacking the FITC label or employing a non-labeled antibody in the procedure.

The cells are analyzed using a flow cytometer. A standard optics and filter arrangement for a FITC-generated signal is used (488 nm excitation, 525 nm bandpass filter for emission). The signals to be collected include log and linear FITC fluorescence (525 nm) and light scatter (0° angle and 90° angle) as correlated parameters.

During flow cytometry, the cell passes a laser at a wavelength which generates scattered light and fluorescence signals from the cell. The photomultiplier tube detects the generated photons, and the signal is passed through a digital-to-analog converter. The signal can be amplified. The resultant signals can be displayed either linearly or logarithmically. Logarithmic displays provide better separation of the peaks, whereas linear displays generally provide more sensitivity.

The cells can also be counterstained with a DNA specific dye such as propidium iodide (PI) to measure cellular DNA content simultaneously. If counterstaining is used, the same filter set-up as described above is used (the PI signal is measured using a 610 nm bandpass filter). This set-up will allow determination of cell cycle position and cellular DNA content, as well as quantitation of the hybridized probe signal. The intensity of signal from bound probe per chromosome or cell is proportional to the number of telomeric repeats and to the telomere length. As the signal intensity is measured, the instrument can be programmed to deflect the cells into specific tubes based upon the signal and the corresponding telomere length.

EXAMPLE 4

PCR-Based Telomere Measurement

This example describes a PCR-based method for measuring telomere length. The telomeric DNA is first treated with an exonuclease to generate blunt ends, and then, a double-stranded linker is attached to the 3' end of the telomere. A forward primer complementary to the linker and a subtelomeric return primer complementary to the subtelomeric region of chromosome X and Y are extended by PCR in the presence of nucleotide triphosphates. The long PCR primer extension products are then separated by size on a gel, and size standards on the gel are used to determine telomere length.

Genomic DNA is digested with Bal31 nuclease (4 U/μg DNA, Boehringer Mannheim) for 5 minutes at 30° C. to remove modified nucleotides at the ends of the telomeres and to blunt-end the DNA. Following the digestion, the Bal31 nuclease is inactivated by the addition of 0.2M ethylenebis(oxyethylenenitrilo)-tetraacetic acid (EGTA) to a final concentration of 15 mM. The DNA is then extracted using phenol/chloroform, precipitated with ethanol, and resuspended in 1×T4 DNA polymerase buffer (13×T4 DNA polymerase buffer is composed of 50 mM NaCl, 10 mM Tris-HCl, 10 mM MgCl$_2$, 1 mM dithiothreitol, pH 7.9) to a final DNA concentration of 0.1–0.5 μg/μl. To improve blunt-ending efficiency, the DNA is treated with T4 DNA polymerase (New England Biolabs) in a mixture comprising 0.25 mM dNTPs (0.0625 mM each of DATP, dGTP, dCTP and dTTP) for 30 minutes at 37° C. The T4 DNA polymerase is inactivated by heating for 15 minutes at 65° C. Alternative nucleases and DNA polymerases can be substituted in this reaction, i.e., Mung Bean nuclease or Pfu DNA polymerase. In addition, the Bal31 treatment of the DNA can be eliminated; and the DNA can be treated directly with T4 DNA polymerase in the presence of dNTPs to generate blunt ends.

The double-stranded linker SLIC-II/aSLIC is prepared by adding equimolar amounts of the phosphorylated SLIC-II oligonucleotide, 5'-GGAATTCTGGTCGACGGATCCTGA-3' (SEQ. ID NO.:8), and the non-phosphorylated complementary oligonucleotide aSLIC, 3'-CCTTAAGACCAGCTGCCTAGGACT-5' (SEQ. ID NO.:9), at room temperature, heating to 94° C. for 3–4 minutes, placing the reaction vessel containing the oligonucleotides in a water bath pre-heated to 65°–70° C., and cooling the vessel to room temperature. The annealing efficiency is checked by digesting 0.5 pmol of the prepared linker with EcoRI followed by electrophoretic analysis (15% polyacrylamide gel) of the digestion products and an untreated linker control. The ratio of the single-stranded, double-stranded, and digested double-stranded oligonucleotide bands on the gel provides a measure of the efficiency of the annealing process and a check that annealing is in the correct register.

The double-stranded linker is ligated onto the blunt ends of the DNA by combining, at 16° C., the blunt-ended DNA (0.1–0.5 μg), the phosphorylated linker (SLIC-II/aSLIC, 1 μg), deionized water (17 μl), 10×blunt-end ligation buffer containing 10 mM ATP (2 μl, New England Biolabs), and T4 DNA ligase (1 μl, 400 U, New England Biolabs). The reaction is allowed to proceed for 6–8 hours and then quenched by heat inactivation of the T4 DNA ligase for 15 minutes at 65° C. As a positive control to determine ligation efficiency, a radioactively labeled SLIC-II/aSLIC linker is prepared as above using $^{32}$P-labeled SLIC-II and ligated to T4 DNA polymerase-treated, MboI digested DNA from BJ cells and/or HinfIlRsaI digested DNA from BJ cells.

PCR amplification of the telomeric region is accomplished by combining 0.1 μg of DNA ligated to SLIC II/aSLIC; 5 μl of 2.5 mM dNTPs (0.0625 mM each of dATP, dGTP, dCTP and dTTP) solution; 5 μl of 10×long PCR buffer (20 mM Tris·HCl (pH 9.0), 150 μg/ml BSA, 3.5 mM MgCl$_2$, and 16 mM (NH$_4$)$_2$SO$_4$); 40 pmol of revXpJCTN primer (5'-CTGATWGGTCCACTTTCAGAGGG-3', (SEQ. ID NO.:7)), 1 μl of ExTaqTM DNA polymerase (Oncor); and deionized water to a total volume of 50 μl. The reaction vessel is then transferred to a thermal cycler for 30 cycles, each cycle comprising incubation temperatures and periods of 94° C. for 1 min. and 65° C. for 1 min. and a final incubation at 72° C. for 10 min.

The amplified primer extension products are resolved on a 0.5% agarose gel. The telomere length is determined by comparison of the primer extension products with size standards.

The reagents employed in the examples are commercially available or can be prepared using commercially available instrumentation, methods, or reagents known in the art. The foregoing examples illustrate various aspects of the invention and practice of the methods of the invention. The examples are not intended to provide an exhaustive description of the many different embodiments of the invention. Thus, although the foregoing invention has been described in some detail by way of illustration and example for purposes of clarity of understanding, those of ordinary skill in the art will realize readily that many changes and modifications can be made thereto without departing from the spirit or scope of the appended claims.

We claim:

1. A method for measuring telomere length, said method comprising the steps of:
   (a) contacting denatured chromosomal DNA that has not been fractionated by gel electrophoresis with a labeled probe having a sequence complementary to a telomere repeat sequence under conditions such that said probe hybridizes specifically to telomeric DNA;
   (b) measuring amount of bound probe; and
   (c) correlating said amount of bound probe measured relative to a control of known telomere length with telomere length.

2. The method of claim 1, wherein said DNA is immobilized on a solid support.

3. The method of claim 1, wherein prior to step (b) said DNA is digested with a nuclease.

4. The method of claim 1, wherein said telomere is a human telomere.

5. The method of claim 1, wherein said chromosomal DNA is human chromosomal DNA.

6. The method of claim 5, wherein said chromosomal DNA is from a blood sample.

7. The method of claim 5, wherein said chromosomal DNA is from a tissue sample.

8. The method of claim 5, wherein said chromosomal DNA is from a sperm sample.

9. The method of claim 5, wherein said chromosomal DNA is from a urine sample.

* * * * *